United States Patent
Long et al.

(10) Patent No.: US 10,766,862 B2
(45) Date of Patent: Sep. 8, 2020

(54) CRYSTAL FORM AND SALT FORM OF AND PREPARATION METHOD FOR TYROSINE KINASE INHIBITOR

(71) Applicant: GUANGDONG RAYNOVENT BIOTECH CO., LTD., Shenzhen (CN)

(72) Inventors: Chaofeng Long, Shanghai (CN); Zhengxia Chen, Shanghai (CN); Xiaoxin Chen, Shanghai (CN); Yang Zhang, Shanghai (CN); Zhuowei Liu, Shanghai (CN); Shuhui Chen, Shanghai (CN); Jian Li, Shanghai (CN)

(73) Assignee: Guangdong Raynovent Biotech Co., Ltd., Shenzhen (CN)

( * ) Notice: Subject to any disclaimer, the term of this patent is extended or adjusted under 35 U.S.C. 154(b) by 0 days.

(21) Appl. No.: 16/337,874

(22) PCT Filed: Sep. 29, 2017

(86) PCT No.: PCT/CN2017/104260
§ 371 (c)(1),
(2) Date: Mar. 28, 2019

(87) PCT Pub. No.: WO2018/059534
PCT Pub. Date: Apr. 5, 2018

(65) Prior Publication Data
US 2020/0024235 A1    Jan. 23, 2020

(30) Foreign Application Priority Data
Sep. 30, 2016  (CN) .......................... 2016 1 0871081

(51) Int. Cl.
*C07D 215/233*    (2006.01)

(52) U.S. Cl.
CPC ...... *C07D 215/233* (2013.01); *C07B 2200/13* (2013.01)

(58) Field of Classification Search
CPC ................................................. C07D 215/233
See application file for complete search history.

(56) References Cited

U.S. PATENT DOCUMENTS

2019/0119217 A1*   4/2019   Long ................... C07D 405/14

FOREIGN PATENT DOCUMENTS

| CN | 1308310 C | 4/2007 |
|---|---|---|
| CN | 107115344 A | 9/2017 |
| WO | 2005063739 A1 | 7/2005 |
| WO | 2006004884 A2 | 1/2006 |
| WO | 2016161952 A1 | 10/2016 |

OTHER PUBLICATIONS

International Search Report dated Jan. 10, 2018 issued for related PCT patent app. No. PCT/CN2017/104260.
Judah Folkman et al; Tumor Angiogenesis: Therapeutic Implications, New England Journal of Medicine, 285: 1182-86 (1971).

* cited by examiner

*Primary Examiner* — D Margaret M Seaman
(74) *Attorney, Agent, or Firm* — D'Ambrosio & Menon, PLLC; Usha Menon

(57) ABSTRACT

Disclosed are a crystal form and a salt form of and a preparation method for a tyrosine kinase inhibitor.

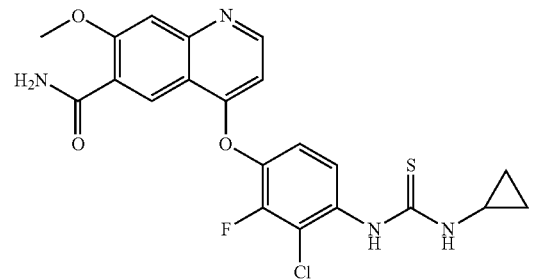

15 Claims, 16 Drawing Sheets

CRYSTAL FORM AND SALT FORM OF AND PREPARATION METHOD FOR TYROSINE KINASE INHIBITOR

CROSS REFERENCE OF RELATED APPLICATION

The present application claims the priority of the Chinese Patent Application No. CN201610871081.1 submitted on Sep. 29, 2016, the content of which is incorporated hereby into the present application.

FIELD OF INVENTION

The present invention relates to a crystal form and a salt form of and a preparation method for a tyrosine kinase inhibitor.

BACKGROUND

Protein tyrosine kinases are a class of enzymes that catalytically transfers phosphate groups from ATPs to tyrosine residues located at a protein substrate, which play a role in normal cell growth. A variety of growth factor receptor proteins act via tyrosine kinases, affect signaling through this process, and in turn regulate cell growth, e.g., FGFR (Fibroblast growth factor receptor), VEGFR (Vascular endothelial growth factor receptor) and PDGFR (Platelet-derived growth factor receptor). However, under certain conditions, these receptors are either mutated or overexpressed, and become abnormal, thereby causing uncontrolled proliferation of cells, resulting in tumor growth, and finally leading to well-known diseases cancers. Growth factor receptor protein tyrosine kinase inhibitors inhibit the phosphorylation process, and act to treat cancers or other diseases characterized by uncontrolled or abnormal cell growth.

Uncontrolled angiogenesis is a mark of cancers. In 1971, Dr. Judah Folkman proposed that the tumor growth depended on angiogenesis (see, Folkman, New England Journal of Medicine, 285: 1182-86 (1971). In accordance with Dr. Folkman, tumors can merely grow to a certain size in absence of additional blood vessels to nourish the tumors. In its simplest statement, the proposals recites that once a tumor "lives (survives)", each increase in tumor cell population must be made by an increase in new capillaries that converge in the tumor. The "living (survival)" of tumor as currently understood refers to the vascular prophase of tumor growth, in which tumor cell population occupying cubic millimeters in volume and containing no more than millions of cells can survive on the existing host microvasculature.

It has indicated that tumors can be treated by inhibiting the angiogenesis, instead of the proliferation of tumor cells themselves. Angiogenesis has been associated with a large number of different types of cancers, including solid tumors and blood-borne tumors. The angiogenesis-associated solid tumors comprise, but are not limited to: rhabdosarcoma, retinoblastoma, Ewing's sarcoma, neuroblastoma, and osteosarcoma. Angiogenesis is associated with breast, prostate, lung, and colon cancers. Angiogenesis is also associated with blood-borne tumors, including any one of leukemia, lymphoma, multiple myeloma, and various acute or chronic bone marrow neoplasms which involve unrestricted proliferation of white blood cells, and are generally accompanied with anemia, decreased blood coagulation, as well as enlargement of lymph nodes, liver, and spleen. It is also believed that angiogenesis plays a role in bone marrow disorders, which cause leukemia, lymphoma and multiple myeloma.

Angiogenesis plays a primary role in cancer metastasis, and if the vasogenic activities can be inhibited or eliminated, tumors would not grow even though they are present. Under the state of disease, the prevention of angiogenesis can reduce damages caused by invasion of new microvasculature. Therapies for controlling vasogenic processes may lead to the elimination or alleviation of these diseases.

Of those, the study of inhibiting angiogenesis by FGFR (Fibroblast growth factor receptor), VEGFR (Vascular endothelial growth factor receptor) and PDGFR (Platelet-derived growth factor receptor) inhibitors tends to be mature.

SUMMARY OF THE PRESENT INVENTION

The present invention provides a crystal form A of Compound 1 which has an X-ray powder diffraction pattern having characteristic diffraction peaks at angles 2θ of: 4.47±0.2°, 7.80±0.2°, 12.61±0.2°.

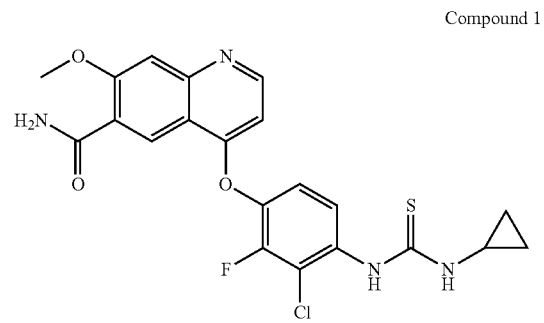 [SMILES: COc1cc2nccc(Oc3ccc(NC(=S)NC4CC4)c(Cl)c3F)c2cc1C(N)=O]

Compound 1

In some embodiments of the present invention, the X-ray powder diffraction pattern of the crystal form A has characteristic diffraction peaks at angles 2θ of: 4.47±0.2°, 7.80±0.2°, 8.87±0.2°, 12.61±0.2°, 13.25±0.2°, 16.32±0.2°, 19.03±0.2°, 26.66±0.2°.

In some embodiments of the present invention, the crystal form A has an XRPD pattern as shown in FIG. 1.

In some embodiments of the present invention, the analytic data of the XRPD pattern of the crystal form A are listed in Table 1:

TABLE 1

The analytic data of the XRPD pattern of the crystal form A

| No. | 2θ (°) | Interplanar Spacing (Å) | Relative Intensity (%) |
|---|---|---|---|
| 1 | 4.466 | 19.7684 | 17.4 |
| 2 | 7.803 | 11.3205 | 17.9 |
| 3 | 8.866 | 9.9654 | 4.9 |
| 4 | 10.938 | 8.0823 | 3.7 |
| 5 | 12.614 | 7.0118 | 100 |
| 6 | 13.246 | 6.6785 | 8.3 |
| 7 | 15.669 | 5.6509 | 2.1 |
| 8 | 16.324 | 5.4256 | 9.7 |
| 9 | 19.027 | 4.6604 | 4.6 |
| 10 | 20.344 | 4.3615 | 2.5 |
| 11 | 21.947 | 4.0466 | 2.6 |
| 12 | 22.5 | 3.9484 | 2.9 |
| 13 | 23.919 | 3.7173 | 3.3 |
| 14 | 25.338 | 3.5121 | 3.6 |
| 15 | 25.695 | 3.4641 | 4.8 |

TABLE 1-continued

The analytic data of the XRPD pattern of the crystal form A

| No. | 2θ (°) | Interplanar Spacing (Å) | Relative Intensity (%) |
|---|---|---|---|
| 16 | 26.286 | 3.3876 | 3.5 |
| 17 | 26.663 | 3.3405 | 12.4 |
| 18 | 27.961 | 3.1883 | 2.4 |
| 19 | 29.206 | 3.0552 | 3.5 |
| 20 | 31.495 | 2.8382 | 4.4 |

In some embodiments of the present invention, the differential scanning calorimetric curve of the crystal form A has a starting point of endothermic peak at 69.00° C.

In some embodiments of the present invention, the crystal form A has a DSC pattern as shown in FIG. 2.

The present invention further provides a crystal form B of Compound 1 which has an X-ray powder diffraction pattern having characteristic diffraction peaks at angles 2θ of: 13.55±0.2°, 22.41±0.2°, 24.16±0.2°.

In some embodiments of the present invention, the X-ray powder diffraction pattern of the crystal form B has characteristic diffraction peaks at angles 2θ of: 13.55±0.2°, 15.94±0.2°, 17.36±0.2°, 22.41±0.2°, 24.16±0.2°, 24.78±0.2°, 25.19±0.2°.

In some embodiments of the present invention, the crystal form B has an XRPD pattern as shown in FIG. 3.

In some embodiments of the present invention, the analytic data of the XRPD pattern of the crystal form B are listed in Table 2:

TABLE 2

The analytic data of the XRPD pattern of the crystal form B

| No. | 2θ (°) | Interplanar Spacing (Å) | Relative Intensity (%) |
|---|---|---|---|
| 1 | 10.292 | 8.5879 | 7.3 |
| 2 | 11.027 | 8.0168 | 17.4 |
| 3 | 13.549 | 6.5298 | 30.2 |
| 4 | 15.028 | 5.8904 | 10 |
| 5 | 15.936 | 5.5567 | 25.9 |
| 6 | 16.365 | 5.4122 | 7 |
| 7 | 17.358 | 5.1045 | 30.2 |
| 8 | 18.043 | 4.9123 | 10.1 |
| 9 | 18.422 | 4.8122 | 8.6 |
| 10 | 19.687 | 4.5057 | 12.4 |
| 11 | 20.551 | 4.3181 | 13.1 |
| 12 | 20.727 | 4.2818 | 10.7 |
| 13 | 22.406 | 3.9646 | 47 |
| 14 | 22.703 | 3.9136 | 22 |
| 15 | 24.163 | 3.6803 | 100 |
| 16 | 24.778 | 3.5903 | 28.4 |
| 17 | 25.189 | 3.5326 | 21.8 |
| 18 | 26.37 | 3.377 | 14.8 |
| 19 | 27.204 | 3.2754 | 4.2 |
| 20 | 27.892 | 3.1961 | 5.9 |
| 21 | 28.918 | 3.085 | 12.2 |
| 22 | 29.431 | 3.0324 | 13.2 |
| 23 | 32.189 | 2.7786 | 6.9 |
| 24 | 38.226 | 2.3525 | 8.2 |

In some embodiments of the present invention, the differential scanning calorimetric curve of the crystal form B has a starting point of endothermic peak at 195.99° C.

In some embodiments of the present invention, the crystal form B has a DSC pattern as shown in FIG. 4.

In some embodiments of the present invention, the thermogravimetric analytic curve of the crystal form B shows a weight loss of 0.6101% at 179.31° C.

In some embodiments of the present invention, the crystal form B has a TGA pattern as shown n FIG. 5.

The present invention further provides a crystal form C of Compound 1 which has an X-ray powder diffraction pattern having characteristic diffraction peaks at angles 2θ of: 16.21±0.2°, 19.84±0.2°, 24.95±0.2°.

In some embodiments of the present invention, the X-ray powder diffraction pattern of the crystal form C has characteristic diffraction peaks at angles 2θ of: 13.29±0.2°, 15.58±0.2°, 16.21±0.2°, 19.84±0.2°, 24.32±0.2°, 24.95±0.2°, 28.13±0.2°.

In some embodiments of the present invention, the crystal form C has an XRPD pattern as shown in FIG. 6.

In some embodiments of the present invention, the analytic data of the XRPD pattern of the crystal form C are listed in Table 3:

TABLE 3

The analytic data of the XRPD pattern of the crystal form C

| No. | 2θ (°) | Interplanar Spacing (Å) | Relative Intensity (%) |
|---|---|---|---|
| 1 | 9.764 | 9.0509 | 17.4 |
| 2 | 10.725 | 8.2422 | 6.1 |
| 3 | 10.925 | 8.0917 | 18.6 |
| 4 | 13.056 | 6.7752 | 45.9 |
| 5 | 13.29 | 6.6566 | 55.7 |
| 6 | 13.938 | 6.3484 | 19.4 |
| 7 | 14.354 | 6.1653 | 23.6 |
| 8 | 15.58 | 5.6829 | 36.6 |
| 9 | 16.207 | 5.4646 | 74.1 |
| 10 | 18.499 | 4.7923 | 15.4 |
| 11 | 19.625 | 4.5198 | 33.3 |
| 12 | 19.84 | 4.4713 | 88.9 |
| 13 | 20.255 | 4.3805 | 8.1 |
| 14 | 20.434 | 4.3425 | 13.7 |
| 15 | 20.862 | 4.2545 | 9.4 |
| 16 | 21.423 | 4.1443 | 31.2 |
| 17 | 23.296 | 3.8152 | 13.7 |
| 18 | 23.41 | 3.7968 | 11.5 |
| 19 | 24.324 | 3.6562 | 49.8 |
| 20 | 24.952 | 3.5656 | 100 |
| 21 | 25.189 | 3.5326 | 37.1 |
| 22 | 25.344 | 3.5114 | 52.2 |
| 23 | 25.543 | 3.4844 | 17.4 |
| 24 | 26.178 | 3.4013 | 8.7 |
| 25 | 26.649 | 3.3423 | 28.9 |
| 26 | 26.985 | 3.3014 | 33 |
| 27 | 27.473 | 3.2438 | 18.5 |
| 28 | 28.129 | 3.1697 | 34 |
| 29 | 28.695 | 3.1085 | 4.6 |
| 30 | 28.916 | 3.0852 | 6.7 |
| 31 | 29.529 | 3.0225 | 12 |
| 32 | 30.178 | 2.959 | 15.1 |
| 33 | 30.521 | 2.9265 | 11.6 |
| 34 | 31.662 | 2.8236 | 5 |
| 35 | 37.149 | 2.4182 | 14 |
| 36 | 38.705 | 2.3245 | 8.9 |
| 37 | 38.822 | 2.3177 | 7.2 |

In some embodiments of the present invention, the differential scanning calorimetric curve of the crystal form C has a starting point of endothermic peak at 197.02° C.

In some embodiments of the present invention, the crystal form C a DSC pattern as shown in FIG. 7.

In some embodiments of the present invention, the thermogravimetric analytic curve of the crystal form C shows a weight loss of 0.4391% at 174.95° C.

In some embodiments of the present invention, the crystal form C has a TGA pattern as shown in FIG. 8.

The present invention further provides a crystal form D of Compound 1 which has an X-ray powder diffraction pattern having characteristic diffraction peaks at angles 2θ of: 6.70±0.2°, 11.30±0.2°.

In some embodiments of the present invention, the X-ray powder diffraction pattern of the crystal form D has characteristic diffraction peaks at angles 2θ of: 6.70±0.2°, 11.30±0.2°, 11.76±0.2°, 15.52±0.2°, 16.35±0.2°, 27.26±0.2°.

In some embodiments of the present invention, the crystal form D has an XRPD pattern as shown in FIG. 9.

In some embodiments of the present invention, the analytic data of the XRPD pattern of the crystal form D are listed in Table 4:

TABLE 4

The analytic data of the XRPD pattern of the crystal form D

| No. | 2θ (°) | Interplanar Spacing (Å) | Relative Intensity (%) |
|---|---|---|---|
| 1 | 6.703 | 13.1766 | 71.6 |
| 2 | 7.713 | 11.4532 | 19.3 |
| 3 | 11.3 | 7.8241 | 100 |
| 4 | 11.756 | 7.5213 | 74.4 |
| 5 | 12.444 | 7.1071 | 23.1 |
| 6 | 15.52 | 5.7047 | 25.6 |
| 7 | 16.349 | 5.4173 | 33.3 |
| 8 | 19.058 | 4.6528 | 14 |
| 9 | 21.524 | 4.125 | 13.3 |
| 10 | 22.436 | 3.9594 | 10.2 |
| 11 | 24.954 | 3.5654 | 18.4 |
| 12 | 25.86 | 3.4424 | 19.3 |
| 13 | 27.264 | 3.2682 | 33.8 |

In some embodiments of the present invention, the differential scanning calorimetric curve of the crystal form D has a starting point of endothermic peak at 145.26° C. and a starting point of endothermic peak at 161.57° C.

In some embodiments of the present invention, the crystal form D has a DSC pattern as shown in FIG. 10.

In some embodiments of the present invention, the thermogravimetric analytic curve of the crystal form D shows a weight loss of 3.409% at 156.50° C.

In some embodiments of the present invention, the crystal form D has a TGA pattern as shown in FIG. 11.

The present invention further provides a crystal form E of Compound 1 which has an X-ray powder diffraction pattern having characteristic diffraction peaks at angles 2θ of: 4.51±0.2°, 11.79±0.2°.

In some embodiments of the present invention, the X-ray powder diffraction pattern of the crystal form E has characteristic diffraction peaks at angles 2θ of: 4.51±0.2°, 6.68±0.2°, 11.79±0.2°, 13.62±0.2°, 15.51±0.2°.

In some embodiments of the present invention, the crystal form E has an XRPD pattern as shown in FIG. 12.

In some embodiments of the present invention, the analytic data of the XRPD pattern of the crystal form E are listed in Table 5:

TABLE 5

The analytic data of the XRPD pattern of the crystal form E

| No. | 2θ (°) | Interplanar Spacing (Å) | Relative Intensity (%) |
|---|---|---|---|
| 1 | 4.506 | 19.5919 | 47.4 |
| 2 | 6.676 | 13.23 | 42.5 |
| 3 | 7.604 | 11.617 | 17.7 |
| 4 | 11.786 | 7.5023 | 100 |
| 5 | 13.621 | 6.4957 | 41.4 |
| 6 | 15.514 | 5.7068 | 30.2 |
| 7 | 18.138 | 4.8867 | 20.1 |
| 8 | 27.313 | 3.2625 | 17.1 |

In some embodiments of the present invention, the differential scanning calorimetric curve of the crystal form E has a starting point of endothermic peak at 143.41° C. and a starting point of endothermic peak at 162.39° C.

In some embodiments of the present invention, the crystal form E has a DSC pattern as shown in FIG. 13.

In some embodiments of the present invention, the thermogravimetric analytic curve of the crystal form E shows a weight loss of 1.121% at 159.86° C.

In some embodiments of the present invention, the crystal form E has a TGA pattern as shown in FIG. 14.

The present invention further provides hydrochloride, p-toluenesulfonate, ethanesulfonate, and methanesulfonate salts of Compound 1.

In some embodiments of the present invention, the salts of Compound 1 are selected from the group consisting of:

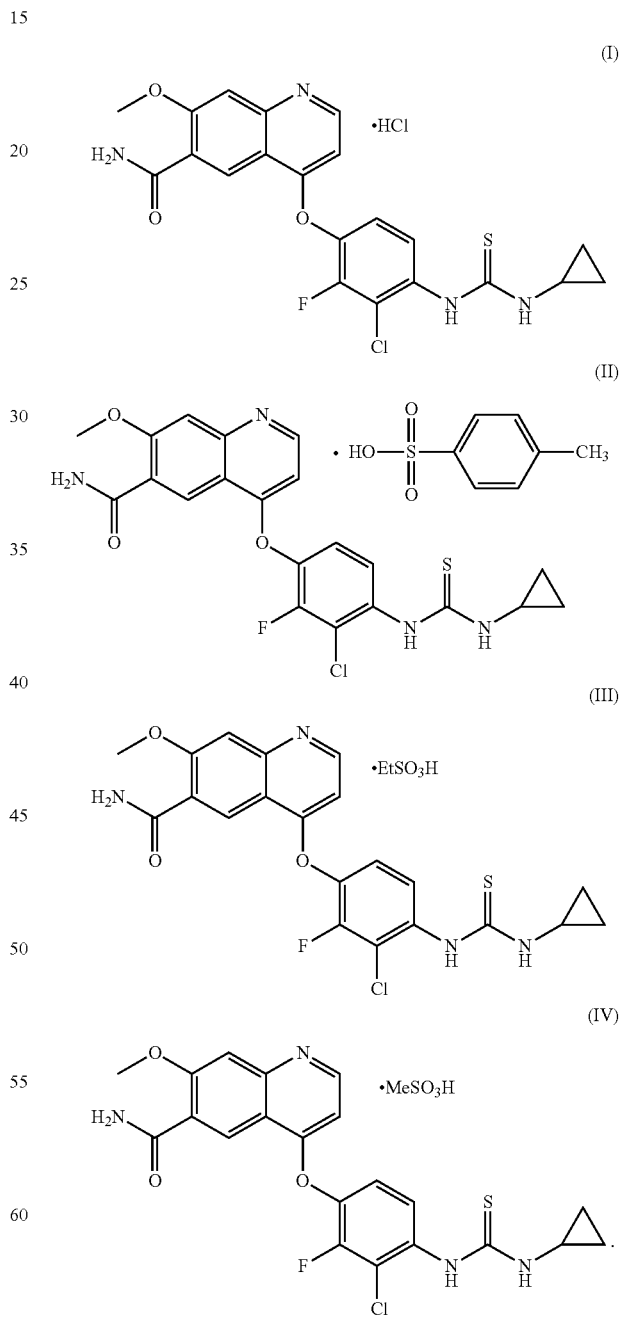

The present invention further provides a crystal form F of the Compound of Formula (I) which has an X-ray powder diffraction pattern having characteristic diffraction peaks at angles 2θ of: 13.32±0.2°, 24.22±0.2°.

In some embodiments of the present invention, the X-ray powder diffraction pattern of the crystal form F has characteristic diffraction peaks at angles 2θ of: 11.64±0.2°, 13.32±0.2°, 14.02±0.2°, 16.78±0.2°, 20.06±0.2°, 24.22±0.2°, 25.02±0.2°.

In some embodiments of the present invention, the crystal form F has an XRPD pattern as shown in FIG. 15.

In some embodiments of the present invention, the analytic data of the XRPD pattern of the crystal form F are listed in Table 6:

TABLE 6

The analytic data of XRPD pattern of the crystal form F

| No. | 2θ (°) | Interplanar Spacing (Å) | Relative Intensity (%) |
|---|---|---|---|
| 1 | 11.645 | 7.5927 | 36.3 |
| 2 | 13.321 | 6.6412 | 70.3 |
| 3 | 14.017 | 6.3129 | 49.1 |
| 4 | 14.406 | 6.1432 | 43.2 |
| 5 | 16.777 | 5.28 | 38.7 |
| 6 | 19.382 | 4.5759 | 34.6 |
| 7 | 20.561 | 4.316 | 33 |
| 8 | 21.058 | 4.2153 | 38.7 |
| 9 | 22.139 | 4.0119 | 21.4 |
| 10 | 22.758 | 3.9042 | 41.2 |
| 11 | 23.385 | 3.8009 | 30.8 |
| 12 | 24.215 | 3.6724 | 100 |
| 13 | 25.025 | 3.5554 | 61.3 |
| 14 | 25.242 | 3.5253 | 46.4 |
| 15 | 26.462 | 3.3654 | 26.1 |
| 16 | 27.478 | 3.2433 | 11.6 |
| 17 | 28.375 | 3.1427 | 34 |
| 18 | 28.912 | 3.0857 | 31.8 |
| 19 | 31.598 | 2.8292 | 16.5 |
| 20 | 32.521 | 2.7509 | 20.4 |

In some embodiments of the present invention, the differential scanning calorimetric curve of the crystal form F has a starting point of endothermic peak at 203.05° C.

In some embodiments of the present invention, the crystal form F has a DSC pattern as shown in FIG. 16.

In some embodiments of the present invention, the thermogravimetric analytic curve of the crystal form F shows a weight loss of 0.8580% at 155.80° C.

In some embodiments of the present invention, the crystal form F has a TGA pattern as shown in FIG. 17.

The present invention further provides a crystal form G of the compound of Formula (II) which has an X-ray powder diffraction pattern having characteristic diffraction peaks at angles 2θ of: 4.84±0.2°, 19.48±0.2°.

In some embodiments of the present invention, the X-ray powder diffraction pattern of the crystal form G has characteristic diffraction peaks at angles 2θ of: 4.84±0.2°, 9.93±0.2°, 15.43±0.2°, 19.48±0.2°, 19.93±0.2°, 20.56±0.2°, 24.20±0.2°, 24.89±0.2°.

In some embodiments of the present invention, the crystal form G has an XRPD pattern as shown in FIG. 18.

In some embodiments of the present invention, the analytic data of the XRPD pattern of the crystal form G are listed in Table 7:

TABLE 7

Analytic Data of XRPD Pattern of Crystal Form G

| No. | 2θ (°) | Interplanar Spacing (Å) | Relative Intensity (%) |
|---|---|---|---|
| 1 | 4.84 | 18.2437 | 100 |
| 2 | 9.661 | 9.147 | 8.4 |
| 3 | 9.934 | 8.8962 | 31.5 |
| 4 | 10.763 | 8.213 | 19.2 |
| 5 | 12.081 | 7.3196 | 15.2 |
| 6 | 12.811 | 6.9042 | 20.8 |
| 7 | 15.434 | 5.7365 | 39.2 |
| 8 | 15.987 | 5.539 | 26.7 |
| 9 | 16.223 | 5.4592 | 15.3 |
| 10 | 18.233 | 4.8617 | 21 |
| 11 | 19.482 | 4.5527 | 41.2 |
| 12 | 19.93 | 4.4513 | 33.1 |
| 13 | 20.563 | 4.3157 | 45 |
| 14 | 21.16 | 4.1953 | 27.4 |
| 15 | 21.653 | 4.1007 | 25.1 |
| 16 | 22.895 | 3.881 | 16.5 |
| 17 | 23.76 | 3.7417 | 28.2 |
| 18 | 24.196 | 3.6753 | 34.4 |
| 19 | 24.884 | 3.5751 | 41.1 |
| 20 | 25.812 | 3.4488 | 21.8 |
| 21 | 26.62 | 3.3459 | 8.4 |
| 22 | 27.452 | 3.2463 | 12.9 |
| 23 | 27.963 | 3.1881 | 14.9 |
| 24 | 29.685 | 3.007 | 16.4 |

In some embodiments of the present invention, the differential scanning calorimetric curve of the crystal form G has a starting point of endothermic peak at 186.93° C.

In some embodiments of the present invention, the crystal form G has a DSC pattern as shown in FIG. 19.

In some embodiments of the present invention, the thermogravimetric analytic curve of the crystal form G shows a weight loss of 1.174% at 166.17° C.

In some embodiments of the present invention, the crystal form G has a TGA pattern as shown in FIG. 20.

The present invention further provides a crystal form H of the compound of Formula (III), wherein the X-ray powder diffraction pattern of the crystal form H has characteristic diffraction peaks at angles 2θ of: 7.80±0.2°, 21.90±0.2°.

In some embodiments of the present invention, the X-ray powder diffraction pattern of the crystal H has characteristic diffraction peaks at angles 2θ of: 7.80±0.2°, 12.53±0.2°, 13.11±0.2°, 14.86±0.2°, 17.78±0.2°, 20.11±0.2°, 21.90±0.2°.

In some embodiments of the present invention, the crystal form H has an XRPD pattern as shown in FIG. 21.

In some embodiments of the present invention, the analytic data of the XRPD pattern of the crystal H are listed in Table 8:

TABLE 8

The analytic data of the XRPD pattern of the crystal form H

| No. | 2θ (°) | Interplanar Spacing (Å) | Relative Intensity (%) |
|---|---|---|---|
| 1 | 7.801 | 11.3235 | 48.6 |
| 2 | 12.534 | 7.0566 | 27.5 |
| 3 | 13.109 | 6.7481 | 17 |
| 4 | 14.863 | 5.9555 | 55.8 |
| 5 | 17.784 | 4.9834 | 29.3 |
| 6 | 20.111 | 4.4117 | 19.3 |
| 7 | 21.076 | 4.2117 | 33.9 |
| 8 | 21.905 | 4.0542 | 100 |
| 9 | 24.571 | 3.62 | 21.3 |

In some embodiments of the present invention, the differential scanning calorimetric curve of the crystal form H has a starting point of endothermic peak at 179.33° C.

In some embodiments of the present invention, the crystal form H has a DSC pattern as shown in FIG. 22.

In some embodiments of the present invention, the thermogravimetric analytic curve of the crystal form H shows a weight loss of 1.336% at 159.12° C.

In some embodiments of the present invention, the crystal form H has a TGA pattern as shown in FIG. 23.

The present invention further provides a crystal form J of the compound of Formula (IV) which has an X-ray powder diffraction pattern having characteristic diffraction peaks at angles 2θ of: 7.88±0.2°, 22.00±0.2°.

In some embodiments of the present invention, the X-ray powder diffraction pattern of the crystal form J has characteristic diffraction peaks at angles 2θ of: 7.88±0.2°, 12.58±0.2°, 15.02±0.2°, 16.42±0.2°, 20.41±0.2°, 21.28±0.2°, 22.00±0.2°, 27.35±0.2°.

In some embodiments of the present invention, the crystal form J has an XRPD pattern as shown in FIG. 24.

In some embodiments of the present invention, the analytic data of the XRPD pattern of the crystal form J are listed in Table 9:

TABLE 9

The analytic data of the XRPD pattern of the crystal form J

| No. | 2θ (°) | Interplanar Spacing (Å) | Relative Intensity (%) |
|---|---|---|---|
| 1 | 7.88 | 11.2103 | 8.1 |
| 2 | 8.94 | 9.8836 | 1.8 |
| 3 | 11.725 | 7.5415 | 1.5 |
| 4 | 12.578 | 7.032 | 4.4 |
| 5 | 13.286 | 6.6587 | 2 |
| 6 | 15.021 | 5.8931 | 15.7 |
| 7 | 16.424 | 5.3929 | 6.9 |
| 8 | 17.983 | 4.9286 | 5.5 |
| 9 | 20.408 | 4.3482 | 6.9 |
| 10 | 21.275 | 4.1729 | 12.8 |
| 11 | 21.611 | 4.1087 | 6.2 |
| 12 | 22.004 | 4.0361 | 20.1 |
| 13 | 22.716 | 3.9112 | 2.3 |
| 14 | 23.518 | 3.7796 | 1.8 |
| 15 | 24.511 | 3.6288 | 2.8 |
| 16 | 24.886 | 3.575 | 5 |
| 17 | 25.379 | 3.5066 | 3 |
| 18 | 27.352 | 3.2579 | 6.6 |
| 19 | 28.023 | 3.1815 | 3.9 |
| 20 | 30.075 | 2.9689 | 2.6 |
| 21 | 34.532 | 2.5952 | 1.8 |

In some embodiments of the present invention, the differential scanning calorimetric curve of the crystal form J has a starting point of endothermic peak at 194.02° C.

In some embodiments of the present invention, the crystal form J has a DSC pattern as shown in FIG. 25.

In some embodiments of the present invention, the thermogravimetric analytic curve of the crystal form J shows a weight loss of 1.717% at 172.21° C.

In some embodiments of the present invention, the crystal form J has a TGA pattern as shown in FIG. 26.

The present invention further provides a crystal form K of the compound of Formula (DI) which has an X-ray powder diffraction pattern having characteristic diffraction peaks at angles 2θ of: 20.35±0.2°, 22.10±0.2°.

In some embodiments of the present invention, the X-ray powder diffraction pattern of the crystal form K has characteristic diffraction peaks at angles 2θ of: 8.02±0.2°, 15.14±0.2°, 16.52±0.2°, 20.35±0.2°, 22.10±0.2°.

In some embodiments of the present invention, the X-ray powder diffraction pattern of the crystal form K has characteristic diffraction peaks at angles 2θ of: 8.02±0.2°, 15.14±0.2°, 16.52±0.2°, 18.10±0.2°, 20.35±0.2°, 21.36±0.2°, 22.10±0.2°, 23.27±0.2°.

In some embodiments of the present invention, the crystal form K has an XRPD pattern as shown in FIG. 27.

In some embodiments of the present invention, the analytic data of the XRPD pattern of the crystal form K are listed in Table 10:

TABLE 10

The analytic data of the XRPD pattern of the crystal form K

| No. | 2θ (°) | Interplanar Spacing (Å) | Relative Intensity (%) |
|---|---|---|---|
| 1 | 8.024 | 11.0094 | 33.9 |
| 2 | 8.974 | 9.8458 | 10.1 |
| 3 | 9.816 | 9.0033 | 29.8 |
| 4 | 10.845 | 8.1515 | 10.4 |
| 5 | 11.828 | 7.476 | 9.2 |
| 6 | 12.734 | 6.9459 | 26.6 |
| 7 | 13.388 | 6.6082 | 15.2 |
| 8 | 14.553 | 6.0816 | 7.9 |
| 9 | 15.14 | 5.8472 | 69 |
| 10 | 16.524 | 5.3604 | 43.8 |
| 11 | 17.23 | 5.1422 | 13.9 |
| 12 | 17.484 | 5.0682 | 9.8 |
| 13 | 18.101 | 4.8967 | 36.9 |
| 14 | 18.412 | 4.8146 | 9.2 |
| 15 | 19.517 | 4.5445 | 8 |
| 16 | 20.35 | 4.3603 | 78.5 |
| 17 | 20.861 | 4.2548 | 49.5 |
| 18 | 21.355 | 4.1573 | 57.3 |
| 19 | 21.709 | 4.0903 | 31.7 |
| 20 | 22.103 | 4.0183 | 100 |
| 21 | 22.816 | 3.8944 | 28.7 |
| 22 | 23.266 | 3.82 | 62.8 |
| 23 | 23.563 | 3.7726 | 17.4 |
| 24 | 24.61 | 3.6144 | 15.3 |
| 25 | 25.001 | 3.5588 | 38.9 |
| 26 | 25.436 | 3.4988 | 24.4 |
| 27 | 25.972 | 3.4279 | 10.5 |
| 28 | 27.41 | 3.2512 | 33.7 |
| 29 | 27.726 | 3.2149 | 19.7 |
| 30 | 28.179 | 3.1642 | 10.3 |
| 31 | 28.655 | 3.1127 | 5 |
| 32 | 29.245 | 3.0512 | 6.9 |
| 33 | 29.914 | 2.9845 | 24.3 |
| 34 | 30.899 | 2.8916 | 9.7 |
| 35 | 31.966 | 2.7974 | 9.6 |
| 36 | 34.602 | 2.5901 | 12.6 |
| 37 | 35.358 | 2.5365 | 9.3 |
| 38 | 36.44 | 2.4636 | 6.4 |
| 39 | 37.721 | 2.3828 | 9.4 |

In some embodiments of the present invention, the differential scanning calorimetric curve of the crystal form K has a starting point of endothermic peak at 202.24° C.

In some embodiments of the present invention, the crystal form K has a DSC pattern as shown in FIG. 28.

The present invention further provides a crystal form L of the compound of Formula (IV) which has an X-ray powder diffraction pattern having characteristic diffraction peaks at angles 2θ of: 21.35±0.2°, 22.05±0.2°.

In some embodiments of the present invention, the X-ray powder diffraction pattern of the crystal form L has characteristic diffraction peaks at angles 2θ of: 8.00±0.2°, 15.10±0.2°, 18.06±0.2°, 21.35±0.2°, 22.05±0.2°.

In some embodiments of the present invention, the X-ray powder diffraction pattern of the crystal form L has characteristic diffraction peaks at angles 2θ of: 8.00±0.2°, 15.10±0.2°, 16.49±0.2°, 18.06±0.2°, 20.49±0.2°, 21.35±0.2°, 22.05±0.2°, 24.94±0.2°.

In some embodiments of the present invention, the crystal form L has an XRPD pattern as shown in FIG. 29.

In some embodiments of the present invention, the analytic data of the XRPD pattern of the crystal form L are listed in Table 11:

TABLE 11

Analytic Data of XRPD Pattern of crystal form L

| No. | 2θ (°) | Interplanar Spacing (Å) | Relative Intensity (%) |
|---|---|---|---|
| 1 | 8.002 | 11.0394 | 43.3 |
| 2 | 8.99 | 9.8283 | 9.6 |
| 3 | 9.754 | 9.0605 | 7.1 |
| 4 | 11.788 | 7.5009 | 16.5 |
| 5 | 12.695 | 6.9674 | 30.3 |
| 6 | 13.363 | 6.6206 | 17.2 |
| 7 | 15.103 | 5.8614 | 63.8 |
| 8 | 16.486 | 5.3728 | 56 |
| 9 | 18.06 | 4.9078 | 42.7 |
| 10 | 20.31 | 4.3689 | 40.1 |
| 11 | 20.486 | 4.3317 | 45.3 |
| 12 | 20.782 | 4.2707 | 11.7 |
| 13 | 21.354 | 4.1576 | 72.7 |
| 14 | 21.652 | 4.101 | 35.7 |
| 15 | 22.047 | 4.0285 | 100 |
| 16 | 22.677 | 3.9179 | 20.2 |
| 17 | 22.795 | 3.8978 | 21.1 |
| 18 | 23.113 | 3.8449 | 7.9 |
| 19 | 23.523 | 3.7788 | 16.5 |
| 20 | 24.55 | 3.623 | 16.7 |
| 21 | 24.944 | 3.5667 | 38.6 |
| 22 | 25.381 | 3.5063 | 20.2 |
| 23 | 26.764 | 3.3282 | 6.2 |
| 24 | 27.37 | 3.2558 | 33.9 |
| 25 | 27.686 | 3.2194 | 14.4 |
| 26 | 28.063 | 3.177 | 15.7 |
| 27 | 28.596 | 3.119 | 6.5 |
| 28 | 30.129 | 2.9637 | 10.6 |
| 29 | 30.802 | 2.9004 | 9.3 |
| 30 | 32.379 | 2.7627 | 5.1 |
| 31 | 33.859 | 2.6452 | 5.4 |
| 32 | 34.51 | 2.5968 | 13.5 |
| 33 | 35.334 | 2.5381 | 6.2 |
| 34 | 36.385 | 2.4672 | 9 |
| 35 | 37.627 | 2.3885 | 8.4 |
| 36 | 39.497 | 2.2797 | 4.6 |

In some embodiments of the present invention, the differential scanning calorimetric curve of the crystal form L has a starting point of endothermic peak at 209.66° C.

In some embodiments of the present invention, the crystal form L has a DSC pattern as shown in FIG. 30.

The present invention further provides a crystal form of the compound of Formula (IV) which has an X-ray powder diffraction pattern having characteristic diffraction peaks at angles 2θ of: 20.78±0.2°, 23.15±0.2°.

In some embodiments of the present invention, the X-ray powder diffraction pattern of the crystal form M has characteristic diffraction peaks at angles 2θ of: 9.68±0.2°, 17.37±0.2°, 18.24±0.2°, 20.19±0.2°, 20.78±0.2°, 22.10±0.2°, 22.74±0.2°, 23.15±0.2°, 29.82±0.2°.

In some embodiments of the present invention, the crystal form M has an XRPD pattern as shown in FIG. 31.

In some embodiments of the present invention, the analytic data of the XRPD pattern of the crystal form M are listed in Table 12:

TABLE 12

The analytic data of the XRPD pattern of the crystal form M

| No. | 2θ (°) | Interplanar Spacing (Å) | Relative Intensity (%) |
|---|---|---|---|
| 1 | 9.681 | 9.1283 | 56.2 |
| 2 | 10.703 | 8.2592 | 17.6 |
| 3 | 11.374 | 7.773 | 10.4 |
| 4 | 12.929 | 6.8417 | 11.2 |
| 5 | 14.474 | 6.1146 | 7.1 |
| 6 | 15.324 | 5.7774 | 6.1 |
| 7 | 15.731 | 5.6288 | 10.6 |
| 8 | 16.562 | 5.348 | 14.6 |
| 9 | 17.112 | 5.1774 | 20.2 |
| 10 | 17.369 | 5.1014 | 22 |
| 11 | 18.239 | 4.8601 | 24.7 |
| 12 | 18.674 | 4.7477 | 8.8 |
| 13 | 19.341 | 4.5854 | 14.4 |
| 14 | 20.188 | 4.395 | 52.4 |
| 15 | 20.784 | 4.2703 | 94.1 |
| 16 | 21.396 | 4.1495 | 18.1 |
| 17 | 22.103 | 4.0183 | 55.6 |
| 18 | 22.736 | 3.9078 | 38.2 |
| 19 | 23.15 | 3.8389 | 100 |
| 20 | 23.588 | 3.7687 | 11 |
| 21 | 23.918 | 3.7174 | 10.7 |
| 22 | 24.632 | 3.6113 | 18.8 |
| 23 | 25.144 | 3.5389 | 12.7 |
| 24 | 25.26 | 3.5229 | 11.2 |
| 25 | 25.895 | 3.4379 | 21.8 |
| 26 | 26.106 | 3.4106 | 10.8 |
| 27 | 27.037 | 3.2951 | 13.3 |
| 28 | 27.604 | 3.2287 | 12.2 |
| 29 | 27.884 | 3.197 | 14.6 |
| 30 | 28.258 | 3.1556 | 4.2 |
| 31 | 28.749 | 3.1027 | 2.6 |
| 32 | 29.103 | 3.0658 | 11.9 |
| 33 | 29.64 | 3.0115 | 25.9 |
| 34 | 29.816 | 2.9941 | 27.6 |
| 35 | 30.301 | 2.9472 | 2.6 |
| 36 | 30.84 | 2.897 | 8.6 |
| 37 | 32.027 | 2.7923 | 13 |
| 38 | 32.461 | 2.7559 | 4.8 |
| 39 | 32.676 | 2.7383 | 6.5 |
| 40 | 34.507 | 2.597 | 4.6 |
| 41 | 35.18 | 2.5489 | 9.7 |
| 42 | 35.65 | 2.5164 | 2.8 |
| 43 | 37.626 | 2.3886 | 5 |
| 44 | 38.276 | 2.3495 | 3.8 |
| 45 | 39.222 | 2.295 | 11.2 |

In some embodiments of the present invention, the differential scanning calorimetric curve of the crystal form M has a starting point of endothermic peak at 219.65° C.

In some embodiments of the present invention, the crystal form M has a DSC pattern as shown in FIG. 32.

Technical Effect

The Compound 1 and its salts of the present invention have not only stable and controllable salt-forming crystal forms, but also the methanesulfonate salt thereof has good solubility in SGF. Thus, Compound 1 and its salts have good prospect in medicine.

Definition and Explanation

Unless otherwise stated, the following terms and phrases as used herein are intended to have the following meanings. Without particular definition, a particular phrase or term should not be considered indefinite or unclear, but should be understood as having general meaning in the art. When a trade name is used herein, it is intended to mean the corresponding product or its active ingredient.

The intermediate compounds of the present invention can be prepared in accordance with various synthesis methods which are well known by persons skilled in the art, including the embodiments as listed below, embodiments formed by the combination of those embodiments with other chemical synthesis methods, and equivalent alternatives which are well known to those skilled in the art. The preferred embodiments comprise, but are not limited to the examples of the present invention.

The chemical reactions of the embodiments of the he present invention are performed in a suitable solvent for the chemical changes of the present invention and the required reagents and materials. To obtain the compounds of the present invention, persons skilled in art sometimes need to make modifications or selection to the synthesis steps or the reaction process based on the existing embodiments.

The present invention will be particularly described by way of examples. These examples are not intended to limit the present invention in any manner.

All the solvents as used in the present invention are commercially available, and directly used without further purification.

The solvents used in the present invention are commercially available. The following abbreviations are used in the present invention: DCM represents dichloromethane; DMF represents N,N-dimethylformamide; DMSO represents dimethylsulfoxide; EtOH represents ethanol; MeOH represents methanol; TFA represents trifluoroacetic acid; TsOH represents p-toluene sulfonic acid; mp represents melting point; $EtSO_3H$ represents ethane sulfonic acid; $MeSO_3H$ represents methane sulfonic acid; ATP represents triphosadenine; HEPES represents 4-hydroxyethylpiperazine ethane sulfonic acid; EGTA represents ethylene glycol-bis-(2-aminoethylether) tetraacetic acid; $MgCl_2$ represents magnesium chloride; $MnCl_2$ represents manganese chloride; DTT represents dithiothreitol.

X-Ray Powder Diffractometer (XRPD)
Instrument Model: Bruker D8 advance X-ray diffractometer
Test Method: About 10-20 mg sample for XRPD detection.
The XRPD parameters are detailed as below:
Light pipe: Cu, kα, (λ=1.54056 Å).
Tube voltage: 40 kV, tube current: 40 mA
Divergence slit: 0.60 mm
Detector slit: 10.50 mm
Anti-scatter slit: 7.10 mm
Scanning range: 4-40 deg (or 2-40 deg)
Step size: 0.02 deg
Step length: 0.12 sec
Rotation speed of sample tray: 15 rpm
Differential Scanning calorimeter (DSC)
Instrument Model: TA Q2000 differential scanning calorimeter
Test Method: A sample (1 mg) was weighed and placed in a DSC aluminum sample cell for testing. The sample was heated from 25° C. to 300° C. at a heating rate of 10° C./min under 50 mL/min $N_2$.
Thermal Gravimetric Analyzer (TGA)
Instrument Model: TA Q5000IR thermal gravimetric analyzer
Test Method: A sample (2-5 mg) was weighed and placed in a TGA platinum sample cell for testing. The sample was heated from room temperature to 20% weight loss at a heating rate of 10° C./min under 25 mL/min $N_2$.

DETAILED DESCRIPTION OF THE INVENTION

Figure 1:
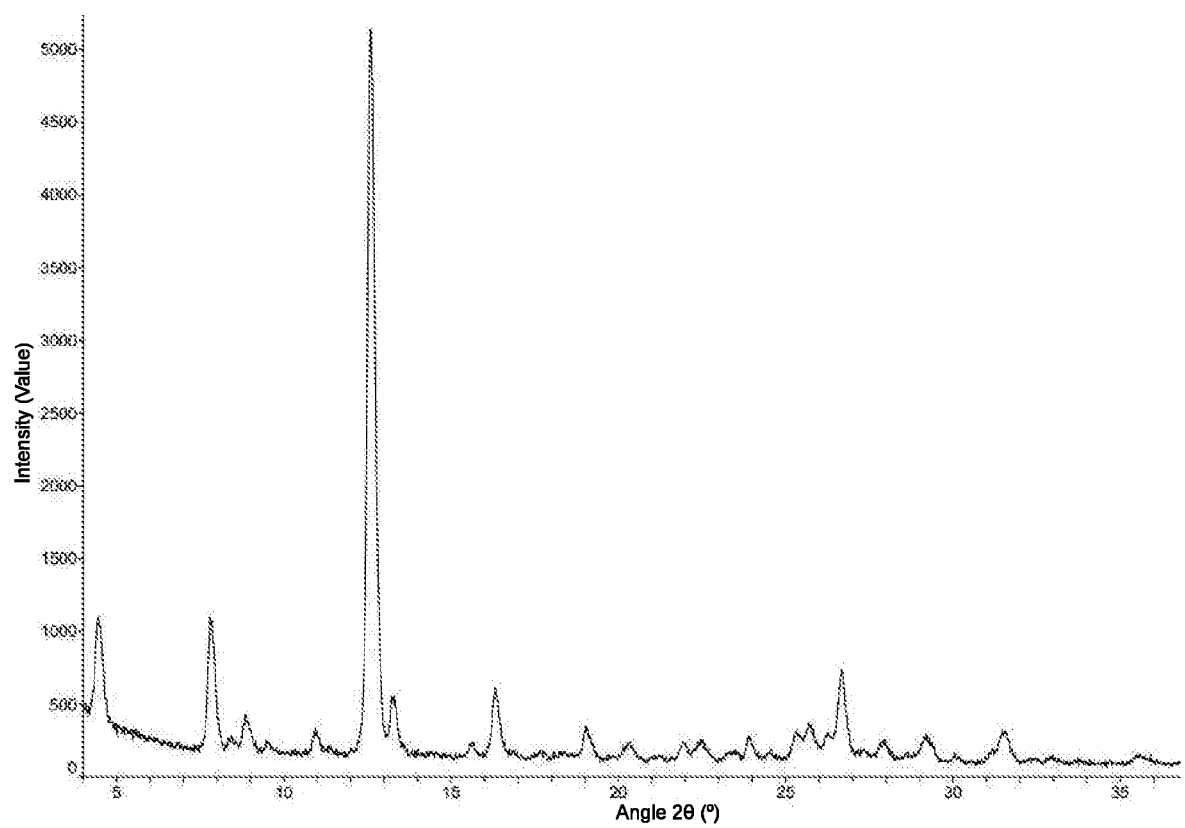
FIG. 1 is an XRPD pattern of the crystal form A with Cu-Kα radiation.
Figure 2:
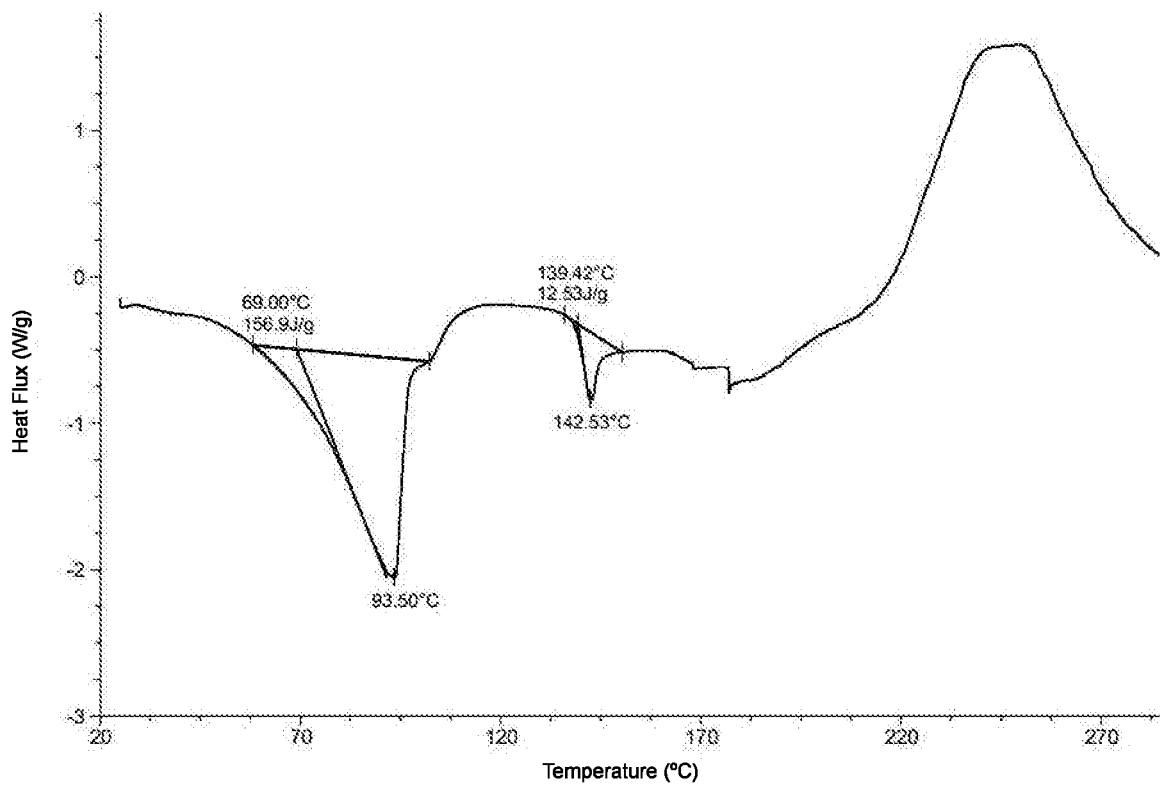
FIG. 2 is a DSC pattern of the crystal form A.

In order to better understand the present invention, the disclosure is further illustrated by the particular examples. However, the particular embodiments are not intended to limit the present invention.

Example 1: Preparation of Crystal Form A of Compound 1

Synthesis Route:

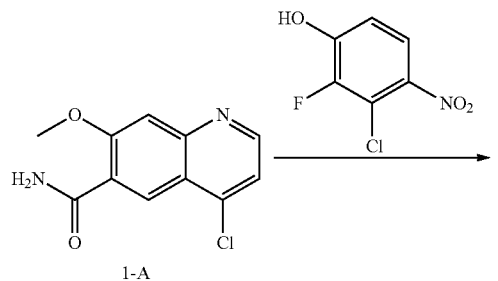

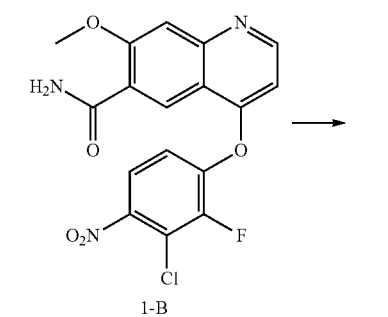

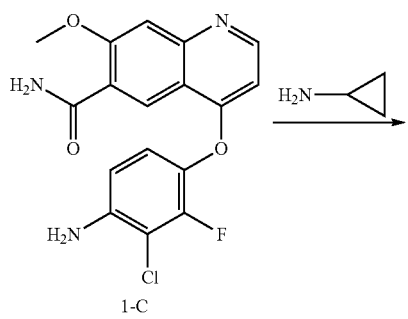

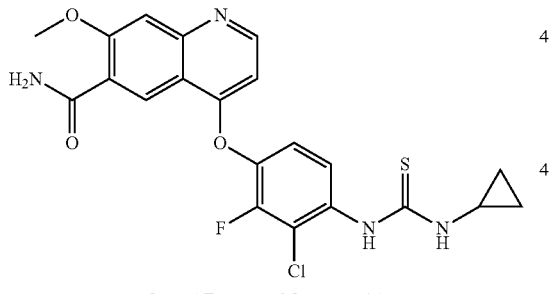

Crystal Form A of Compound 1

1. Preparation of Compound 1-B

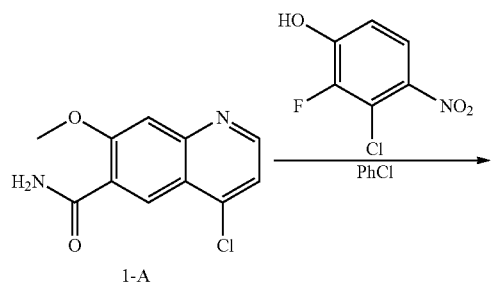

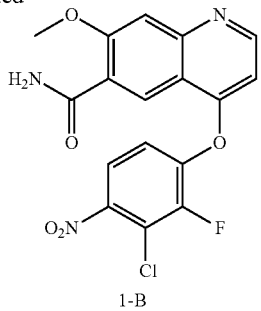

Compound 1-A (40.00 g, 169.03 mmol) and 3-chloro-2-fluoro-4-nitrophenol (48.56 g, 253.55 mmol) were added into a flask containing chlorobenzene (500 mL). The flask was heated to 140° C. and stirred for 3 hr. LCMS showed that the reaction was complete, and the heating was stopped. The reaction mixture was cooled to 20° C., and stirred at 20° C. for additional 15 hr. A large amount of solids were precipitated, filtered, and dried to give the target product crude 1-B (78 g, yellow solid), which was directly used for next step.

$^1$H NMR (400 MHz, DMSO-d-6) δ 9.02 (d, J=6.0 Hz, 2H), 8.68 (s, 1H), 7.96 (d, J=13.6 Hz, 1H), 7.75 (s, 1H), 741-7.35 (m, 1H), 7.22-7.10 (m, 1H), 4.07 (s, 3H)

2. Preparation of Compound 1-C

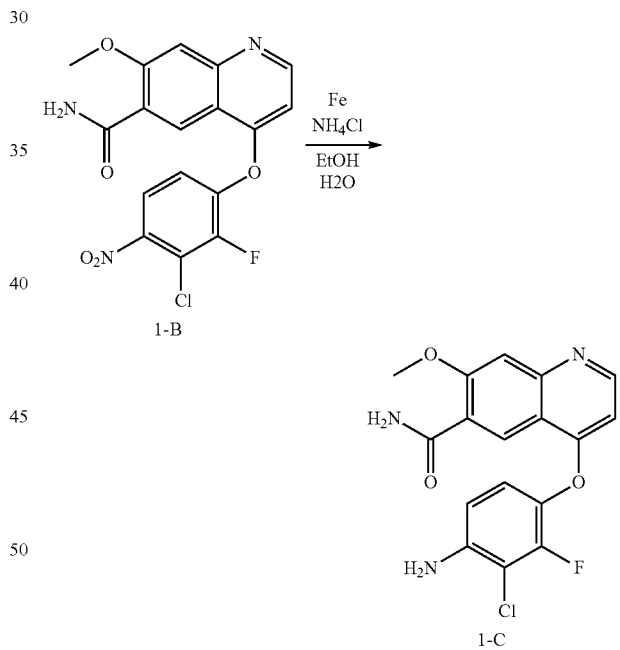

Compound 1-B (78.00 g, 199.11 mmol) was added into a flask containing a mixture of ethanol (700 mL) and water (140 mL). Under stirring, iron powders (33.36 g, 597.33 mmol) and ammonium chloride (42.60 g, 796.44 mmol) were added into the flask. The reaction mixture was purged with nitrogen gas three times, heated to 90° C. and stirred for 2 hr. LCMS showed that the reaction was complete. The reaction mixture was cooled to 50° C. and filtered. The filter cake was washed with ethanol (200 mL*3) and a mixture of methane dichloride and isopropanol (200 mL*5, 3/1), respectively. The filtrates were combined and concentrated. The residue was dissolved in a mixture of methane dichloride and isopropanol (3 L, 3/1), and then washed with a solution of sodium hydroxide (300 mL*3, 0.5N) and saturated brine (300 mL*2), respectively. The organic phase was dried over anhydrous sodium sulfate, and concentrated to give the target product crude 1-C (20.40 g, green solid), which was directly used for next step.

$^1$H NMR (400 MHz, DMSO-d-6) δ 8.67 (d, J=5.2 Hz, 2H), 7.88 (s, 1H), 7.76 (s, 1H), 7.53 (s, 1H), 7.19 (t, J=8.8 Hz, 1H), 6.74 (d, J=9.2 Hz, 1H), 6.51 (d, J=5.2 Hz, 1H), 5.84 (s, 2H), 4.04 (s, 3H)

3. Preparation of Crystal Form A of Compound 1

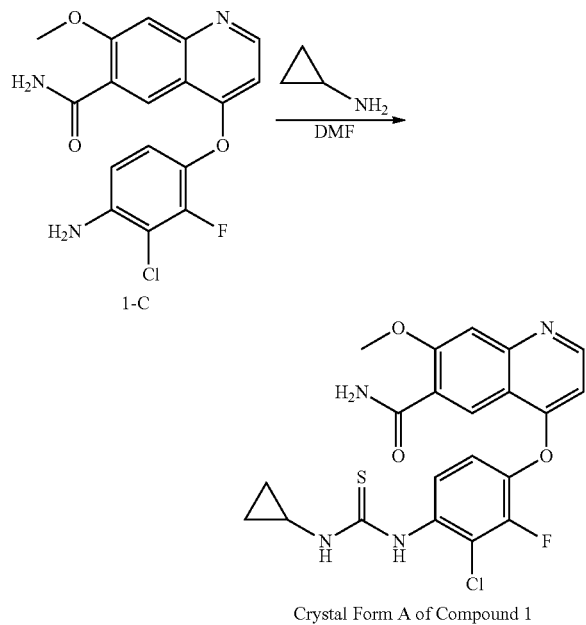

Crystal Form A of Compound 1

Compound 1-C (4.00 g, 11.06 mmol) was added into a flash containing 40 mL DMF, and then pyridine (874.64 mg, 11.06 mmol) and phenyl chlorothionocarbonate (3.44 g, 19.91 mmol) were added into the flask under stirring. The reaction mixture was stirred at 20° C. for 1 hr. Then, cyclopropylamine (1.26 g, 22.12 mmol) was added dropwise into the flask. The reaction mixture was stirred at 20° C. for additional 3 hr. LCMS showed that the raw materials were completely consumed, and substantially converted to the target product. The reaction mixture was quenched with (400 ml). A large amount of solids were precipitated and filtered. The filter cake was washed with water (50 mL*2) to give the target crude product. The crude product was separated by preparative chromatography (trifluoroacetic acid system), and then neutralized with a saturated NaHCO$_3$ (5 mL) to pH=8-9. White solids were precipitated, filtered, and dried to give the target crystal form A of the product (1.00 g, white solid).

$^1$H NMR (400 MHz, METHANOL-d4) δ 9.05 (s, 1H), 8.75 (d, J=6.4 Hz, 1H), 7.75-7.60 (m, 1H), 7.58 (s, 1H), 7.50-7.35 (m, 1H), 6.85-6.75 (m, 1H), 4.15 (s, 3H), 1.05-0.75 (m, 1H).

Preparation of Other Crystal Forms:

Crystal form A (30 mg) was weighed and added into methanol (0.4 mL) to form a suspension. The suspension sample was placed on a magnetic stirrer (40° C.) and shaken for 2 days (in dark). The residual solids were centrifugalized, and dried in a vacuum drying oven at 40° C. overnight. XRPD was used to detect the crystal form, and it was found that the crystal form of the final product was crystal form B.

Crystal form A (30 mg) was weighed and added into ethanol (0.4 mL) to form a suspension. The suspension sample was placed on a magnetic stirrer (40° C.) and shaken for 2 days (in dark). The residual solids were centrifugalized, and dried in a vacuum drying oven at 40° C. overnight. XRPD was used to detect the crystal form, and it was found that the crystal form of the final product was crystal form C.

Crystal form A (30 mg) was weighed and added into isopropanol (0.4 mL) to form a suspension. The suspension sample was placed on a magnetic stirrer (40° C.) and shaken for 2 days (in dark). The residual solids were centrifugalized, and dried in a vacuum drying oven at 40° C. overnight. XRPD was used to detect the crystal form, and it was found that the crystal form of the final product was crystal form D.

Crystal form A (30 mg) was weighed and added into a 3:1 mixture of methanol-water (0.4 mL) to form a suspension. The suspension sample was placed on a magnetic stirrer (40° C.) and shaken for 2 days (in dark). The residual solids were centrifugalized, and dried in a vacuum drying oven at 40° C. overnight. XRPD was used to detect the crystal form, and it was found that the crystal form of the final product was crystal form E.

Crystal form A (50 mg) was weighed and added into acetone (4 mL) for ultrasonic dissolution. After centrifugation, the supernatant was placed on a magnetic stirrer, and then 0.085 mL of hydrochloric acid-acetone solution (V/V, 1:9) was slowly added under stirring. The mixture was stirred at ambient temperature overnight, and centrifugalized. The residual solid sample was placed in a vacuum drying oven (25° C.), and dried overnight. XRPD was used to detect the crystal form, and it was found that the crystal form of the final product was Crystal form F.

Crystal form A (50 mg) was weighed, and added into acetone (4 ml) for ultrasonic dissolution. After centrifugation, the supernatant was placed on a magnetic stirrer, and 0.3 mL of p-toluene sulfonic acid-acetone solution (p-toluene sulfonic acid (19.3 mg) in acetone (0.3 mL)) was slowly added under stirring. The mixture was stirred at ambient temperature overnight, and centrifugalized. The residual solid sample was placed in a vacuum drying oven (25° C.), and dried overnight. XRPD was used to detect the crystal form, and it was found that the crystal form of the final product was crystal form G.

Crystal form A (50 mg) was weighed, and added into acetone (4 ml) for ultrasonic dissolution. After centrifugation, the supernatant was placed on a magnetic stirrer, and then 0.09 mL of ethane sulfonic acid-acetone solution (V/V, 1:9) was slowly added under stirring. The mixture was stirred at ambient temperature overnight, and centrifugalized. The residual solid sample was placed in a vacuum drying oven (25° C.), and dried overnight. XRPD was used to detect the crystal form, and it was found that the crystal form of the final product was crystal form H.

Crystal form A (50 mg) was weighed and added into acetone (4 ml) for ultrasonic dissolution. After centrifugation, the supernatant was placed on a magnetic stirrer, and then 0.07 mL of methane sulfonic acid-acetone solution (V/V, 1:9) was slowly added under stirring. The mixture was stirred at ambient temperature overnight, and centrifugalized. The residual solid sample was placed in a vacuum drying oven (25° C.), and dried overnight. XRPD was used to detect the crystal form, and it was found that the crystal form of the final product was crystal form J.

1 g of methane sulfonic acid was added into 30 mL acetone, and heated to 60° C. 1 g of crystal form A was added in batches into the solution of methane sulfonic acid in acetone. After completion of addition, the mixture was stirred at 60° C. for 5 minutes. Then, the mixture was slowly cooled to 15-20° C., stirred for additional 14 hr, and filtered. The filter cake was washed with acetone (3 mL*2), and dried in vacuum at 30° C. for 8 hr. XRPD was used to detect the crystal form, and it was found that the crystal form of the final product was crystal form K.

12.49 g of methane sulfonic acid was added into 1.5 L of ethanol, and the temperature increased to 35-40° C. (internal temperature). The reaction mixture was heated to 60° C., and crystal form A (50.00 g) was added into the solution of methane sulfonic acid in ethanol. After completion of addition, the mixture was stirred at 60° C. for 1 minute. Then, the mixture was slowly cooled to 15-20° C., stirred for additional 14 hr, and filtered. The filter cake was washed with ethanol (10 mL*2), and dried in vacuum at ambient temperature to give the final product of crystal form L.

251 mg of methane sulfonic acid was dissolved in 20 mL of methanol at 10-15° C. 1.0 g of crystal form A was added under reflux and stirred until being completely dissolved. The heating was stopped. The mixture was gradually cooled to 10-15° C., stirred for 20 hr, filtered, and dried at 60° C. for 24 hr. XRPD was used to detect the crystal form, and it was found that the crystal form of the final product was crystal form M.

Test of Solubility of Crystal Form a of Compound 1 and its Salts

1. Preparation of Diluent and Mobile Phase

Diluent: Acetonitrile as diluent

Mobile phase A: 0.1% aqueous phosphoric acid solution

For stance: 2.0 mL of phosphoric acid was moved and added into 2000 mL of water, subject to ultrasonic treatment for 10 minutes until homogeneous, and cooled to room temperature to give the mobile phase A.

Mobile phase B: Acetonitrile as mobile phase B.

2. Preparation of Control Solution (Crystal Form a as Control Sample)

Crystal form A was accurately weighed and added into a sample vial. 10 mL of acetonitrile was added, and subject to ultrasonic treatment for 5 min. The mixture was cooled to room temperature, and mixed homogeneously. Two aliquots were formulated in parallel, and labelled as STD-1 and STD-2, respectively.

3. Preparation of Linear Solution

The control solution STD-1 was gradually diluted 1×, 5×, 10×, 100×, and 1000×, and labelled as the linear solutions L1, L2, L3, L4, L5.

4. Test of Solubility of Crystal Form a and its Salts

The crystal form A and its salts were tested for their solubility in medias at 4 different pH values. About 10 mg of free base (10.8 mg of hydrochloride, 12.1 mg of methane sulfonate) was added into a glass vial. Four aliquots were weighed, 5.0 mL of individual media (water, SGF, FaSSIF, FeSSIF*) was added to each aliquot, respectively. The mixture was mixed homogeneously to for a suspension. A magnet was placed into the suspension, which was placed on a magnetic stirred for stirring. After 24 hours of stirred, a sample was taken and centrifugalized. The supernatant was detected by HPLC for its concentration and pH value. Of those, the HPLC test method is listed in Table 13.

TABLE 13

Chromatographic Analysis of Compounds

| Column | Ascentis Express C18 (4.6 mm*100 mm, 2.7 μm) | | |
|---|---|---|---|
| Mobile phase | A = 0.1% aqueous phosphoric acid solution | | |
| | B = acetonitrile | | |
| Gradient | Time (min) | A (%) | B (%) |
| | 0 | 90 | 10 |
| | 13 | 5 | 95 |
| | 15 | 5 | 95 |
| Flow Rate | 1.5 mL/min | | |
| Run Time | 15 min (Post time: 3 min) | | |
| Column Temperature | 40° C. | | |
| Injection Volume | 2 μL | | |
| Detection Wavelength | 250 nm | | |

The results of solubility are listed in Table 14.

TABLE 14

Results of Solubility Test of Crystal Form A and Its Salts in Four Medias

| Sample | Test | Water (pH 6.33) | SGF (pH 1.72)* | FaSSIF (pH 6.48) | FeSSIF (pH 4.89) |
|---|---|---|---|---|---|
| Crystal form A | pH (24 hr) | 7.16 | 1.97 | 6.18 | 4.98 |
| | Solubility (ug/mL)_24 hr | 2.38 | 692.77 | 2.62 | 61.24 |
| Hydrochloride Crystal form F | pH (24 hr) | 2.56 | 1.80 | 3.73 | 4.89 |
| | solubility (ug/mL)_24 hr | 319.05 | 1217.07 | 64.32 | 70.12 |
| Methane sulfonate Crystal form K | pH (24 hr) | 2.53 | 1.76 | 3.92 | 4.88 |
| | solubility (ug/mL)_24 hr | 329.78 | 6601.59 | 38.04 | 77.24 |

*5 mL of SGF was added to methane sulfonate to form a solution, to which additional methane sulfonate was added to a concentration corresponding to 10 mg/mL of free base.
*SGF: stimulated gastric fluid; FaSSIF: fasted state stimulated intestinal fluid; FeSSIF: fed state stimulated intestinal fluid.
Conclusion: Crystal form A in a form of free base is almost insoluble or very slightly soluble in water, FaSSIF, and FeSSIF except that it is relatively soluble in SGF. The salt compounds are almost insoluble or very slightly soluble in FaSSIF and FeSSIF, but are relatively soluble in SGF and water. Of those, the methane sulfonate has relatively high solubility in SGF.

Test of Solid Stability of Crystal Form F (Hydrochloride), Crystal Form K (Methane Sulfonate) and Crystal Form L (Methane Sulfonate)

1. Preparation of Solid Stability Sample and Lofting

About 5 mg of each crystal form was accurately weighed and placed in a glass vial. Two aliquots were taken as the sample for test under each condition and at each time point. One aliquot was taken as the sample for XRPD test under each condition and at each time point. The vials containing sample were sealed with aluminum foil, and the foil was pierced to form some holes thereon. Then, the samples were placed in constant temperature & humidity chambers under the conditions of 60° C./92.5% RH and 40° C./75% RH.

TABLE 15

Test of Solid Stability of Compound

| Conditions | 0 day | 5 days | 10 days | 30 days |
|---|---|---|---|---|
| 60° C. (open) | X | X | X | X |
| 92.5% RH (open) | | X | X | X |
| 40° C./75% RH (open) | | X | X | X |

*Items X to be tested: Properties and states, XRPD, contents, and the related substances (TRS).

2. Analysis of Sample of Solid Stability

At the tested time point, the sample was taken out, capped, and stood to room temperature. The sample was observed for any change of its properties and/or the states, subject to XRPD, and analyzed by HPLC for the content and the related substances of the sample. The results of the solid stability are listed in Table 17 and 18.

2.1 Preparation of Mobile Phase and Diluent

Diluent: an aqueous solution of methanol-0.04% TFA (90:10, v:v)

For instance: To 900 mL of methanol was added 100 mL of 0.04% aqueous solution of TFA. The mixture was mixed homogeneously, subject to ultrasonic treatment for 15 minutes, and cooled to room temperature for use as diluent.

Mobile phase A: 0.04% aqueous solution of TFA

For instance: 0.8 mL of TFA was added into 2000 mL. The mixture was mixed homogeneously, subject to ultrasonic treatment for 15 minutes, and cooled to room temperature for use as mobile phase A.

Mobile phase B: Acetonitrile as mobile phase B.

2.2 Preparation of Sample Solution

Crystal form F (hydrochloride): To each sample was added 18 mL of the diluent (to the sample at Day 0 was added 20 mL of the diluent). The mixture was subject to ultrasonic treatment for 2 min, and mixed homogeneously for use as the sample solution.

Crystal forms K and L (methane sulfonate): To each sample was added 15 mL of the diluent. The mixture was subject to ultrasonic treatment for 2 min, and mixed homogeneously for use as the sample solution.

NOTE: All the sample solutions were injected for analysis immediately after formulation.

2.3 Analysis of Sample Solution

Once the HPLC system was stable, the sample was injected for analysis. The analytic methods are listed in Table 16:

TABLE 16

Analytic Methods of Contents of Compound and The Related Substances

| Column | Waters Xbridge Shield RP18 (150*4.6 mm, 3.5 μm) |
|---|---|
| Mobile phase | A: 0.04% aqueous solution of TFA |

TABLE 16-continued

Analytic Methods of Contents of Compound and The Related Substances

| | B: acetonitrile | | |
|---|---|---|---|
| Elution Gradient | Time (min) | A (%) | B (%) |
| | 0 | 90 | 10 |
| | 5 | 90 | 10 |
| | 23 | 82 | 18 |
| | 40 | 45 | 55 |
| | 50 | 20 | 80 |
| | 50.01 | 20 | 80 |
| | 60 | 90 | 10 |
| Run time | 60 min | | |
| Column temperature | 40° C. | | |
| Flow rate | 1.0 mL/min | | |
| Injection volumn | 5 μL | | |
| Detection wavelength | 250 nm | | |
| Diluent/ProbeWash | Methanol: 0.04% TFA (90:10, v/v) | | |

The analysis results are listed in Table 17:

TABLE 17

Test Results of Solid Stability of Crystal Form F (Hydrochloride) and Crystal Form K (Methane Sulfonate) (Day 5 and Day 10) *

| Sample | Conditions | Time points | Appearance | XRPD | Content (%)*[1] | Total impurity (%)*[2] |
|---|---|---|---|---|---|---|
| Crystal form K (Methane sulfonate) | −20° C. | Day 0 | white powders | Crystal form K | 100.0 | 5.20 |
| | 60° C. | Day 5 | white powders | Crystal form K | 94.6 | 9.33 |
| | | Day 10 | | Crystal form K | 93.9 | 8.94 |
| | 92.5% RH | Day 5 | white powders | Crystal form K | 99.3 | 5.16 |
| | | Day 10 | | Crystal form K | 99.5 | 4.87 |
| | 40° C./75% RH | Day 5 | white powders | Crystal form K | 98.5 | 5.32 |
| | | Day 10 | | Crystal form K | 101.7 | 5.62 |
| Crystal form F (Hydrochloride) | −20° C. | Day 0 | white powders | Crystal form F | 100.0 | 4.66 |
| | 60° C. | Day 5 | white powders | Crystal form F | 99.6 | 4.86 |
| | 92.5% RH | | white powders | Crystal form F | 100.3 | 4.52 |
| | 40° C./75% RH | | white powders | Crystal form F | 100.5 | 4.94 |

* The stability sample of hydrochloride at Day 10 is not analyzed.
*[1]The sample at Day 0 is used as the control per se.
*[2]The sum of all the individual impurities of greater than 0.02%.
Conclusion: Crystal form F (hydrochloride) and crystal form K (methane sulfonate) have relative good solid stability.

TABLE 18

Test Results of Solid Stability of Crystal Form L (Methane Sulfonate) (Stability Data at Days 5, 10 and 30) *

| Sample | Conditions | Time point | Appearance | XRPD | Content (%)*[1] | Total impurity (%)*[2] |
|---|---|---|---|---|---|---|
| Crystal form L | −20° C. | Day 0 | white powders | Crystal form L | 97.5 | 0.8 |

TABLE 18-continued

Test Results of Solid Stability of Crystal Form L (Methane Sulfonate) (Stability Data at Days 5, 10 and 30) *

| Sample | Conditions | Time point | Appearance | XRPD | Content (%)*1 | Total impurity (%)*2 |
|---|---|---|---|---|---|---|
| (methane sulfonate) | 60° C. | Day 5 | white powders | Crystal form L | 97.8 | 0.8 |
| | | Day 10 | | Crystal form L | 97.4 | 0.8 |
| | | Day 30 | | Crystal form L | 97.1 | 0.8 |
| | 92.5% RH | Day 5 | white powders | Crystal form L | 98.0 | 0.8 |
| | | Day 10 | | Crystal form L | 97.6 | 0.8 |
| | | Day 30 | | Crystal form L | 100.2 | 0.8 |
| | 40° C./ 75% RH | Day 30 | white powders | Crystal form L | 99.4 | 0.9 |
| | | Day 60 | | Crystal form L | 99.9 | 0.9 |
| | | Day 90 | | Crystal form L | 97.5 | 1.0 |

* The stability sample of hydrochloride at Day 10 is not analyzed.
*[1]The sample at Day 0 is used as the control per se.
*[2]The sum of all the individual impurities of greater than 0.05%.
Conclusion: Crystal Form L (Methane Sulfonate) have relative good solid stability.

Experimental Example 1: Test of In Vitro Enzyme Activity of Compound 1

Object

It is to evaluate the inhibitory effect of the compound on three kinases VEGFR2, FGFR1, PDGFRB by detecting the enzyme activity in accordance with Z'-LYTE™ Detection Kinase Assay and using the ICso value of the compound as the index.

Experimental Materials

Recombinant human VEGFR2 and FGFR1 proteins are purchased from Life technology, and PDGFRB proteinase is purchased from Millipore.
Z-LYTE™ Kit Tyr1 and Tyr4 are purchased from Life technology.
Read with Multimode Microplate Reader Envision (PerkinElmer).
Test Methods
The compound to be test was subject to a 3-fold concentration gradient dilution to 11 final concentrations ranging from 10 μM to 0.17 nM 11 with two duplicate wells per concentration. The concentration of DMSO was 1% in the test reaction.
VEGFR2 Enzyme Reaction:
3 nM VEGFR2 protein kinase, 2 μM Tyr1 peptide, 100 μM ATP, 50 mM HEPES (pH 7.5), 10 mM $MgCl_2$, 1 mM EGTA, 0.01% BRIJ-35. The test plate is Black Proxiplate 384-Plus plate (PerkinElmer). The reaction runs at room temperature for 60 minutes, and the reaction system is 10 μL.
FGFR1 Enzyme Reaction:
1 nM FGFR1 protein kinase, 2 μM Tyr4 peptide, 25 μM ATP, 50 mM HEPES (pH 7.5), 10 mM $MgCl_2$, 1 mM EGTA, 0.01% BRIJ-35, 2 mM $MnCl_2$, 1 mM DTT. The test plate is Black Proxiplate 384-Plus plate (PerkinElmer). The reaction runs at room temperature for 60 minutes, and the reaction system is 10 μL.

PDGFRB Enzyme Reaction:
40 nM PDGFRB protein kinase, 2 μM Tyr4 peptide, 100 μM ATP, 50 mM HEPES (pH 7.5), 10 mM $MgCl_2$, 1 mM EGTA, 0.01% BRIJ-35, 2 mM $MnCl_2$, 1 mM DTT. The test plate is Black Proxiplate 384-Plus plate (PerkinElmer). The reaction runs at room temperature for 60 minutes, and the reaction system is 104.
Reaction Assay:
5 μL of DV reagent B (1:128) was added to the kinase reaction mixture to stopped the reaction. The reaction mixture was incubated at 23° C. for 60 minutes, and read by Envision.
Data Analysis:
The data were converted to the phosphorylation rate and the inhibition rate. The parameter curve was fitted (Model 205 in XLFIT5, iDBS) to obtain the ICso data of the compound. The test results are listed in Table 19:

TABLE 19

Test Results of $IC_{50}$ by Z'-LYTE ™

| Sample (Subject compound) | VEGFR2 | FGFR1 | PDGFRB |
|---|---|---|---|
| Compound 1 | AAA | AA | AAA |

Note:
VEGFR2: AAA < 50 nM.
FGFR1: 50 nM ≤ AA < 200 nM,.
PDGFRB: AAA < 50 nM.

Conclusion:
Compound 1 has superior inhibitory activity on VEGFR2, FGFR1, PDGFRB in vitro.

Experimental Example 2: In Vitro Cytological Inhibitory Activity of Compound 1

Object
It is to detect the intracellular ATP change by CellTiter-Glo® Luminescent Cell Viability Assay, and evaluate the inhibitory effect of the compound on in vitro cell HUVEC with ICso value of the compound as the index.

Experimental Materials

HUVEC cell lines (ATCC), EGM-2 BulletKit (Lonza), hVEGF-165 (Cell Signaling), pancreatin (Invitrogen), DPBS (Hyclone), 384-well cell plate (Greiner), 384-well compound plate (Greiner), CO2 incubator (Thermo), centrifuger (Eppendorf), Vi-cell Cell Count (Beckman Coulter), Bravo Automated Liquid Handing Platform (Agilent), Envision (Perkin Elmer)
Test Method
A. Cells recovery and growth.
B. Cell planking: HUVEC cells were re-suspended with a fasted media (containing only 2% FBS and 0.1% GA-1000), and diluted to a concentration of 20,000/mL. The diluted cells were added into 384-well plate (Greiner) with 50 μL/well. The cell plate was placed in an incubator containing 5% CO2 at 37° C. overnight.
C. Compound Addition: The compound to be tested was subject to a 4-fold gradient dilution to 10 samples having a final concentration ranging from 10 μM to 0.038 nM with two duplicate wells per concentration. 47.6 μL of fasted media was added to each well in the intermediate place, and 2.4 μL of the compound was transferred from the gradient diluted compound plate to the intermediate plate and mixed homogeneously. Then, additional 5 μL of liquid was transferred from the intermediate plate to the cell plate. After incubation in an incubator containing 5% CO2 at 37° for 1 hr, the mixture was added to 5 μL of fasted media containing hVEGF-165 with a final concentration of 20 ng/ml and Heparin with a final concentration 1 ng/mL, and incubated in an incubator containing 5% CO2 at 37° C. for additional 72 hr.

D. After 72 hr, 30 μL of detection agent was added. The mixture was incubated at room temperature for 10-30 minutes, and read with Envision.

Data Processing

The reading were converted to inhibition rate (%) by the following equations: (Max-Sample)/(Max-Min)*100%. The parameter curve was fitted (Model 205 in XLFIT5, iDBS) to obtain the $IC_{50}$ data. The test results are listed in Table 20:

TABLE 20

Test Results of $IC_{50}$ by CellTiter-Glo ®

| Sample (Subject Compound) | HUVEC |
|---|---|
| Compound 1 | AA |

Note:
AA < 100 nM.
Conclusion: Compound 1 has superior inhibitory activity on HUVEC.

Experimental Example 3: Analysis of Tumor Growth Inhibition (TGI)

The development and growth of tumors are evaluated by the relation between the tumor volume and time. The long axis (L) and the short axis (W) are measured with caliper twice per week. The tumor volume (TV) is calculated in accordance with the formula of $(L \times W^2)/2$. TGI is calculated from the difference between the median tumor volume of mice of the solvent group and the median tumor volume of mice of the administration group, and expressed as a percentage relative to the median tumor volume of the solvent group.

It is calculated from the equation of:

% TGH(Median Tumor Volume (Control Group)
Median Tumor Volume (Administration
Group))/Median Tumor Volume (Control
Group))×100%

The initial statistical analysis is carried out by repeated variance analyses. Next, multiple comparisons are made by Scheffe psot hoc test method. A solvent (aqueous solution containing 0.5% of methylcellulose and 0.2% Tween) alone is used as negative control.

The test results are listed in Table 21:

TABLE 21

Test Results of Antitumor Activity of Mice

| | A549 Transplant Model | TGI % (Last Administration) |
|---|---|---|
| Crystal form L of the compound of Formula (IV) | 50 mg/kg, QD | 82 |
| Crystal form L of the compound of Formula (IV) | 100 mg/kg, QD | 90 |
| Crystal form L of the compound of Formula (IV) | 200 mg/kg, QD | 91 |

Conclusion: The crystal form L of the compound of Formula (IV) has superior anti-tumor effect in vivo.

What is claimed is:

1. A crystal form of Compound 1 comprising a crystal form A, a crystal form B, a crystal form C, a crystal form D or a crystal form E,

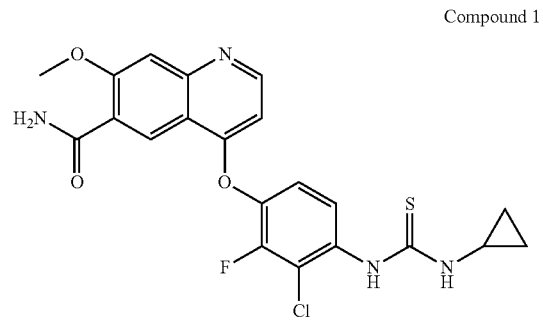 [SMILES: COc1cc2nccc(Oc3ccc(NC(=S)NC4CC4)c(Cl)c3F)c2cc1C(N)=O]

Compound 1 wherein,
the crystal form A has an X-ray powder diffraction pattern with characteristic diffraction peaks at angles 2θ of: 4.47±0.2°, 7.80±0.2°, 12.61±0.2°, 13.25±0.2°, 16.32±0.2°;
the crystal form B has an X-ray powder diffraction pattern with characteristic diffraction peaks at angles 2θ of: 13.55±0.2°, 15.94±0.2°, 17.36±0.2°, 22.41±0.2°, 24.16±0.2°, 24.78±0.2°;
the crystal form C has an X-ray powder diffraction pattern with characteristic diffraction peaks at angles 2θ of: 13.29±0.2°, 15.58±0.2°, 16.21±0.2°, 19.84±0.2°, 24.95±0.2°;
the crystal form D has an X-ray powder diffraction pattern with characteristic diffraction peaks at angles 2θ of: 6.70±0.2°, 11.30±0.2°, 11.76±0.2°, 15.52±0.2°, 16.35±0.2°;
the crystal form E has an X-ray powder diffraction pattern with characteristic diffraction peaks at angles 2θ of: 4.51±0.2°, 6.68±0.2°, 11.79±0.2°, 13.62±0.2°.

2. The crystal form of Compound 1 according to claim 1, wherein
the crystal form A further has an X-ray powder diffraction pattern with characteristic diffraction peaks at angles 2θ of: 4.47±0.2°, 7.80±0.2°, 8.87±0.2°, 12.61±0.2°, 13.25±0.2°, 16.32±0.2°, 19.03±0.2°, 26.66±0.2°;
the crystal form B further has an X-ray powder diffraction pattern with characteristic diffraction peaks at angles 2θ of: 13.55±0.2°, 15.94±0.2°, 17.36±0.2°, 22.41±0.2°, 24.16±0.2°, 24.78±0.2°, 25.19±0.2°;
the crystal form C further has an X-ray powder diffraction pattern with characteristic diffraction peaks at angles 2θ of: 13.29±0.2°, 15.58±0.2°, 16.21±0.2°, 19.84±0.2°, 24.32±0.2°, 24.95±0.2°, 28.13±0.2°;
the crystal form D further has an X-ray powder diffraction pattern with characteristic diffraction peaks at angles 2θ of: 6.70±0.2°, 11.30±0.2°, 11.76±0.2°, 15.52±0.2°, 16.35±0.2°, 27.26±0.2°;
the crystal form E further has an X-ray powder diffraction pattern with characteristic diffraction peaks at angles 2θ of: 4.51±0.2°, 6.68±0.2°, 11.79±0.2°, 13.62±0.2°, 15.51±0.2°.

Figure 3:
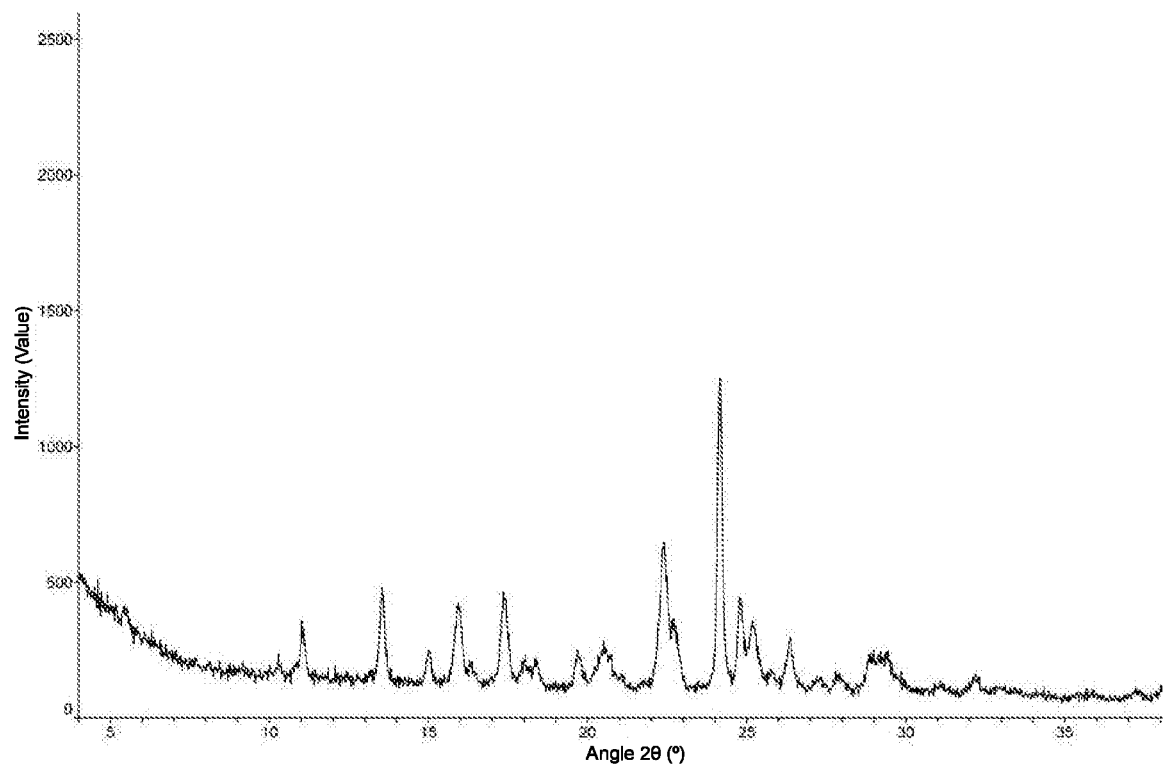
FIG. 3 is an XRPD pattern of the crystal form B with Cu-Kα radiation.
Figure 4:
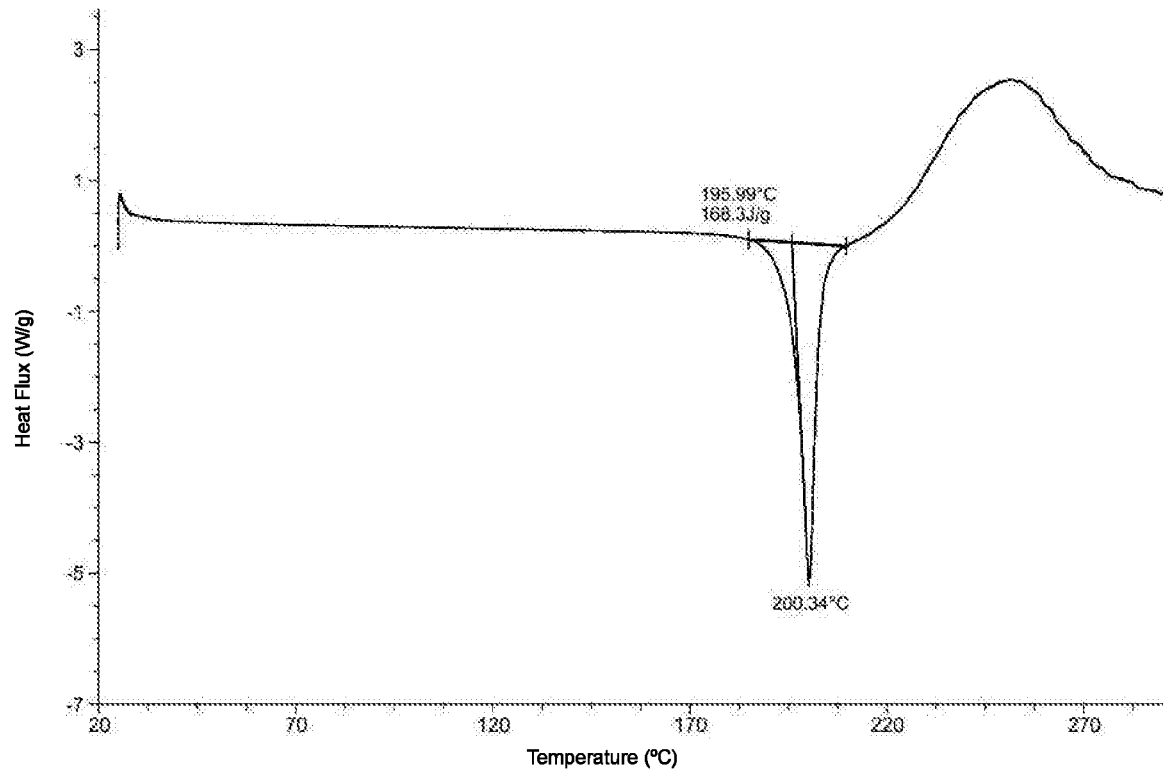
FIG. 4 is a DSC pattern of the crystal form B.
Figure 5:
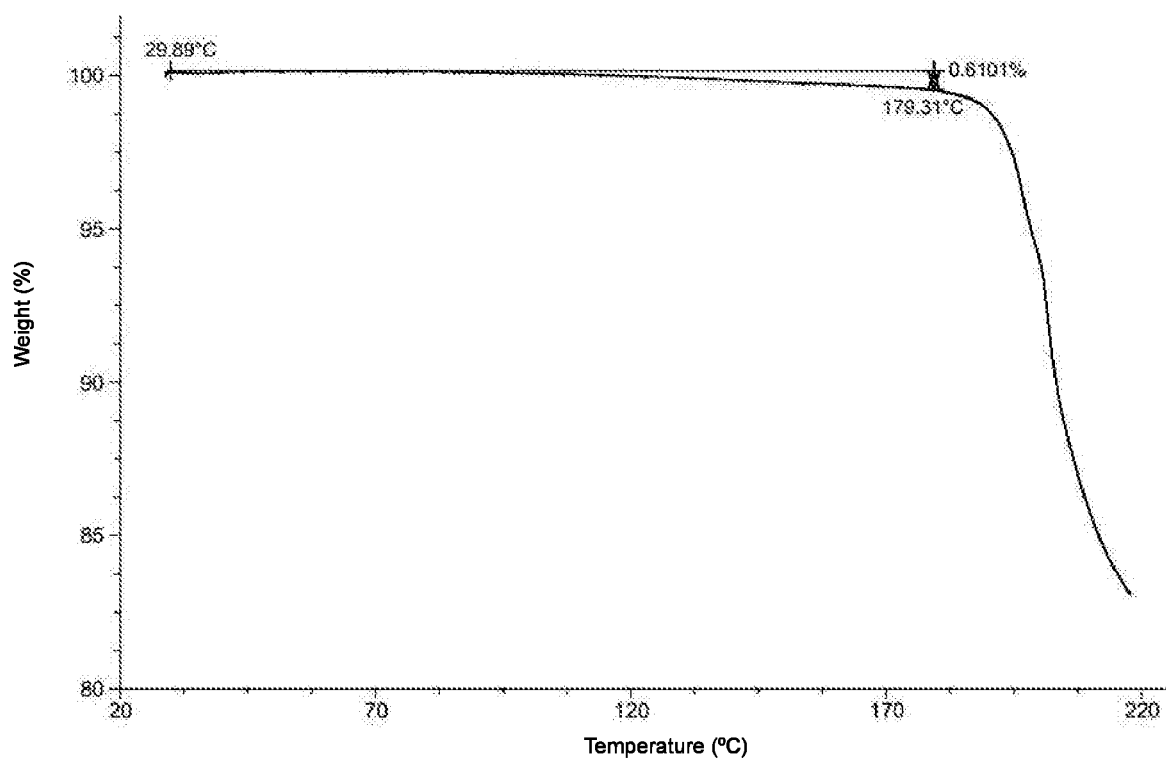
FIG. 5 is a TGA pattern of the crystal form B.
Figure 6:
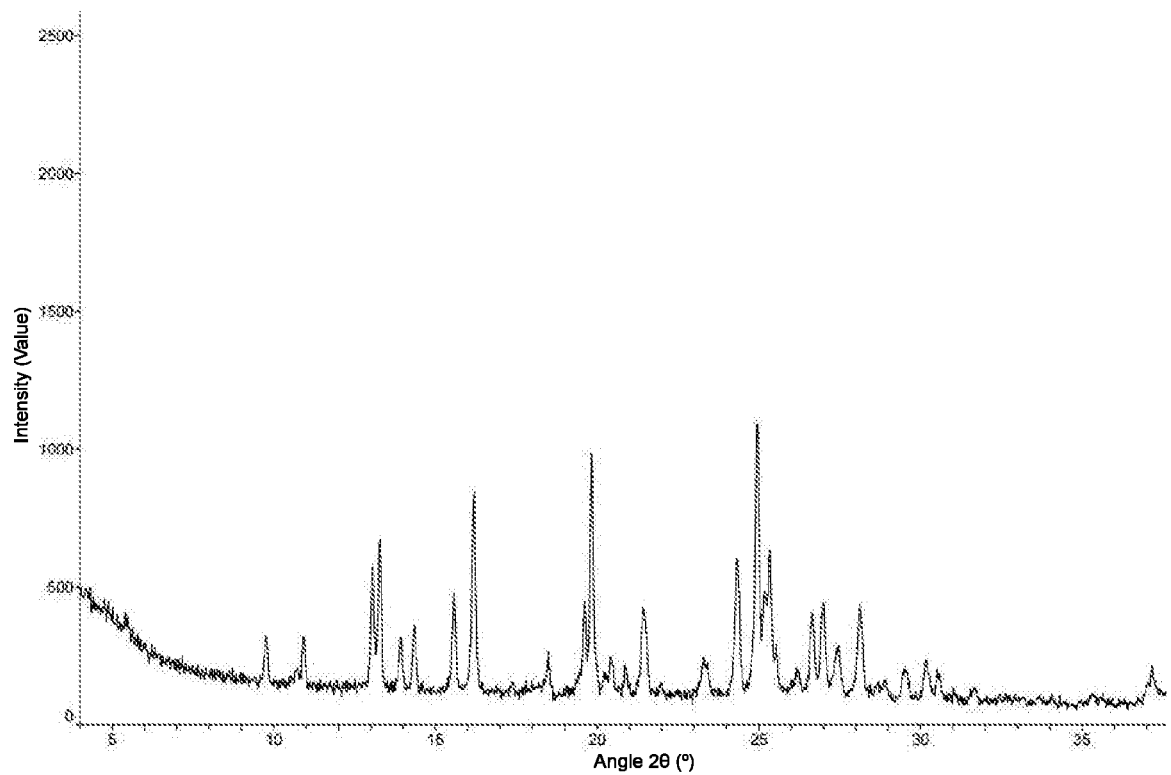
FIG. 6 is an XRPD pattern of the crystal form C with Cu-Kα radiation.
Figure 7:
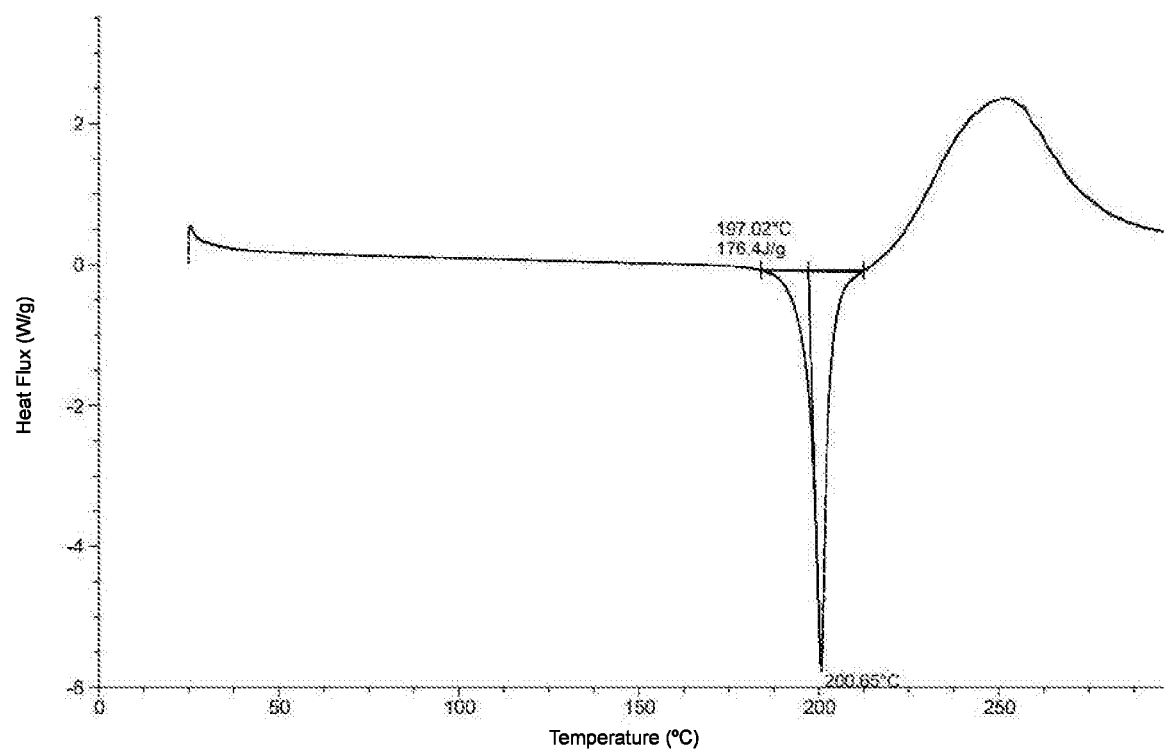
FIG. 7 is a DSC pattern of the crystal form C.
Figure 8:
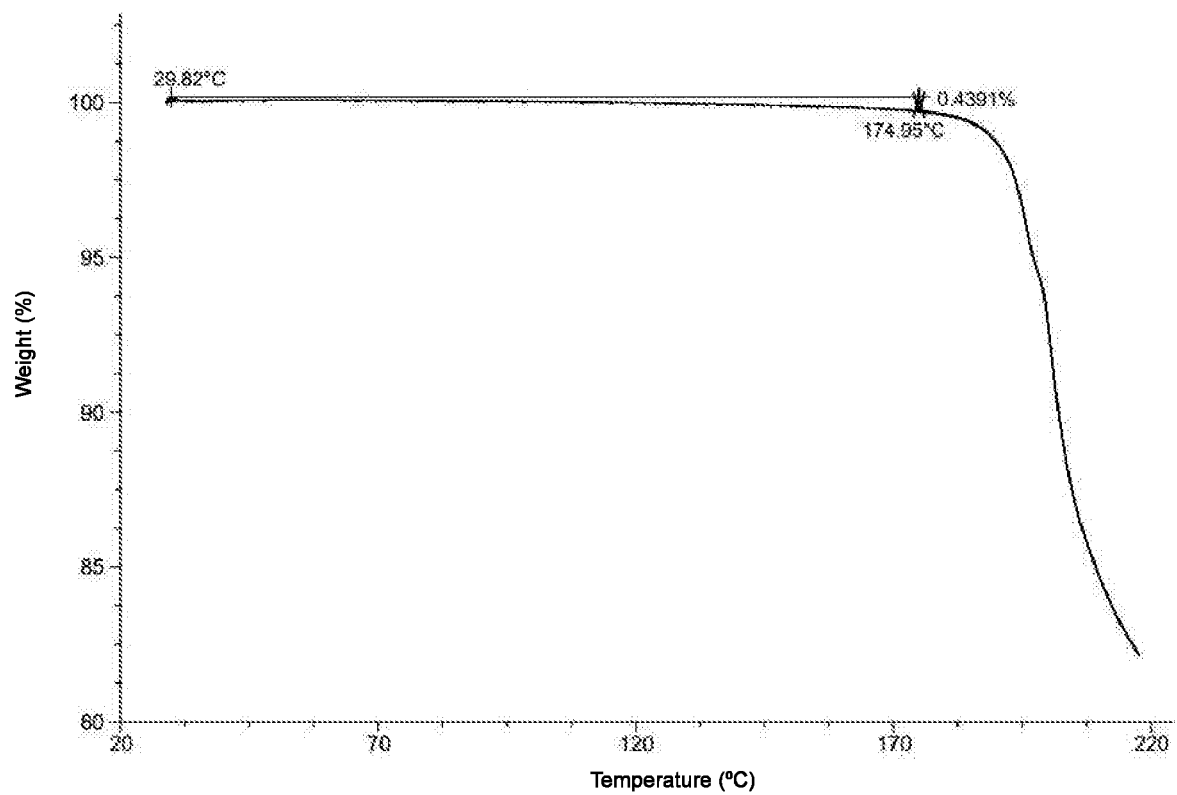
FIG. 8 is a TGA pattern of the crystal form C.
Figure 9:
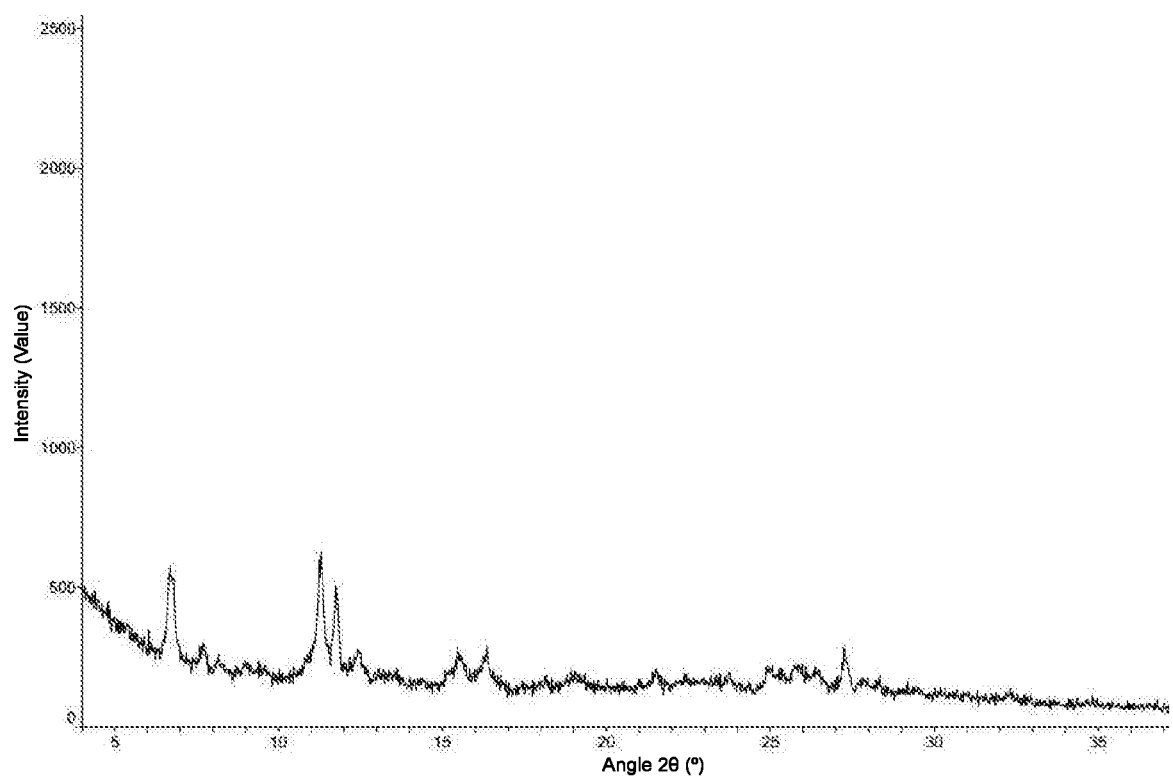
FIG. 9 is an XRPD pattern of the crystal form D with Cu-Kα radiation.
Figure 10:
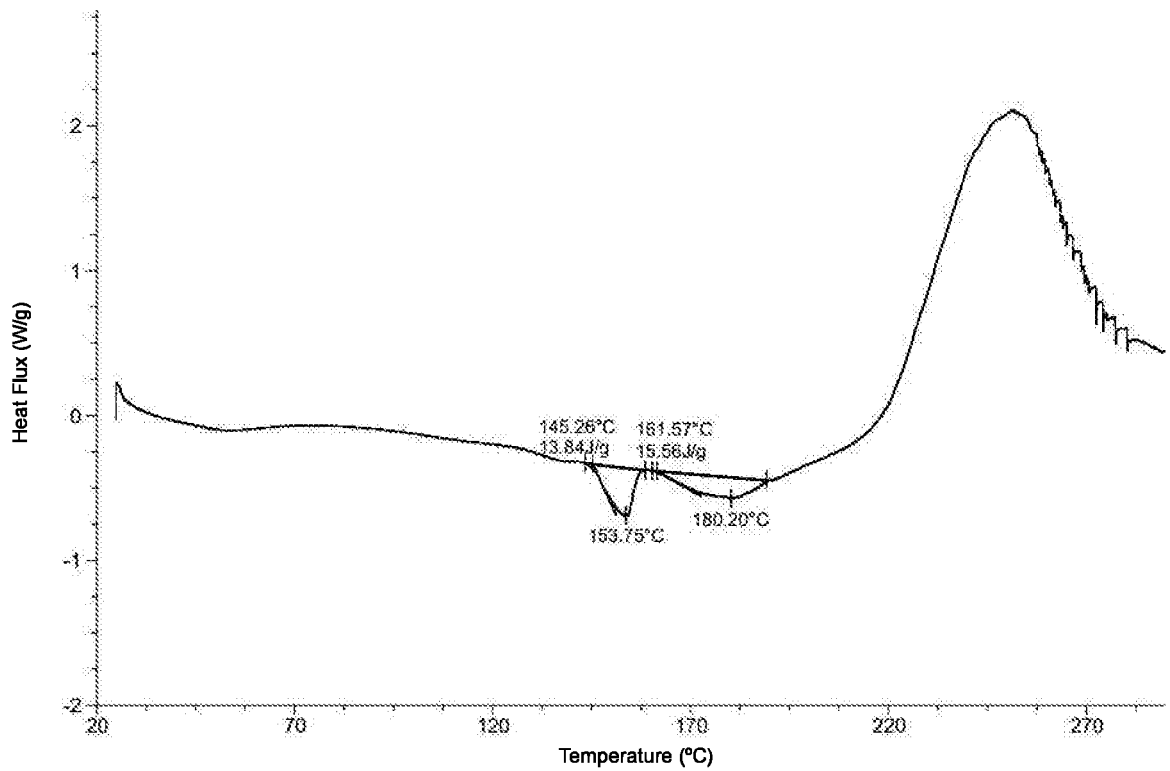
FIG. 10 is a DSC pattern of the crystal form D.
Figure 11:
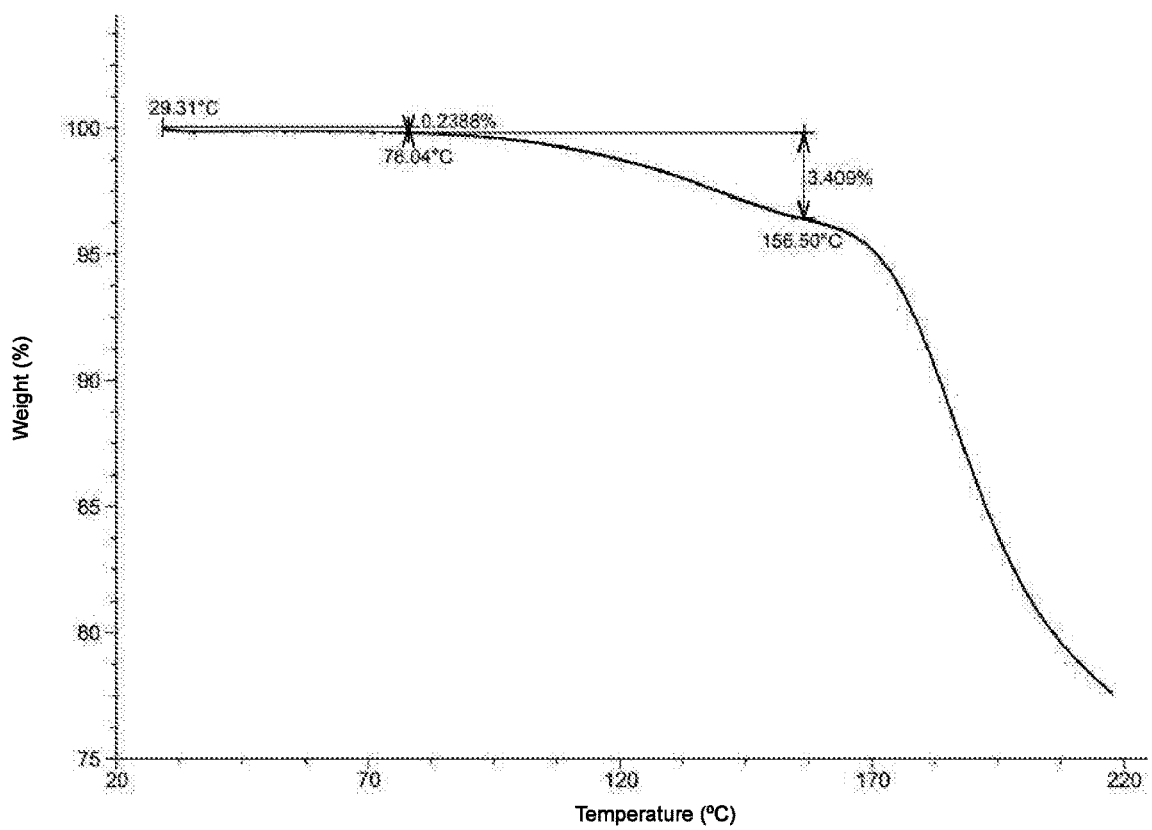
FIG. 11 is a TGA pattern of the crystal form D.
Figure 12:
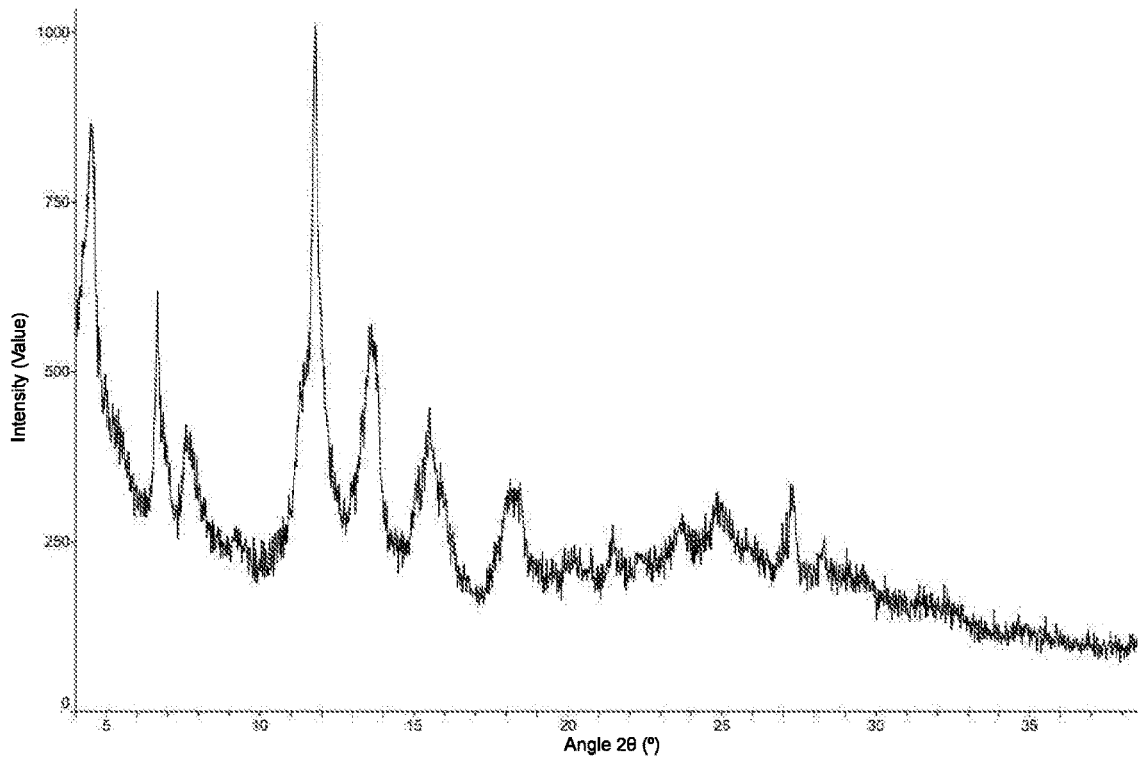
FIG. 12 is an XRPD pattern of the crystal form E with Cu-Kα radiation.
Figure 13:
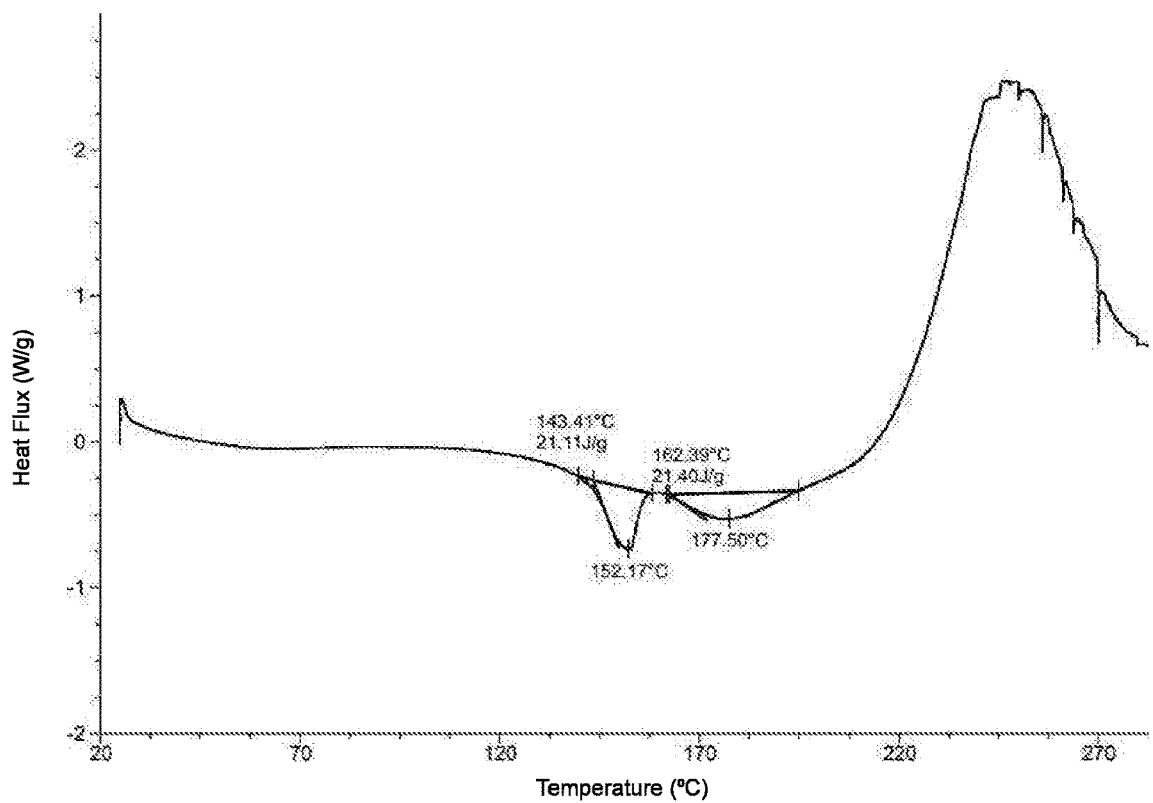
FIG. 13 is a DSC pattern of the crystal form E.
Figure 14:
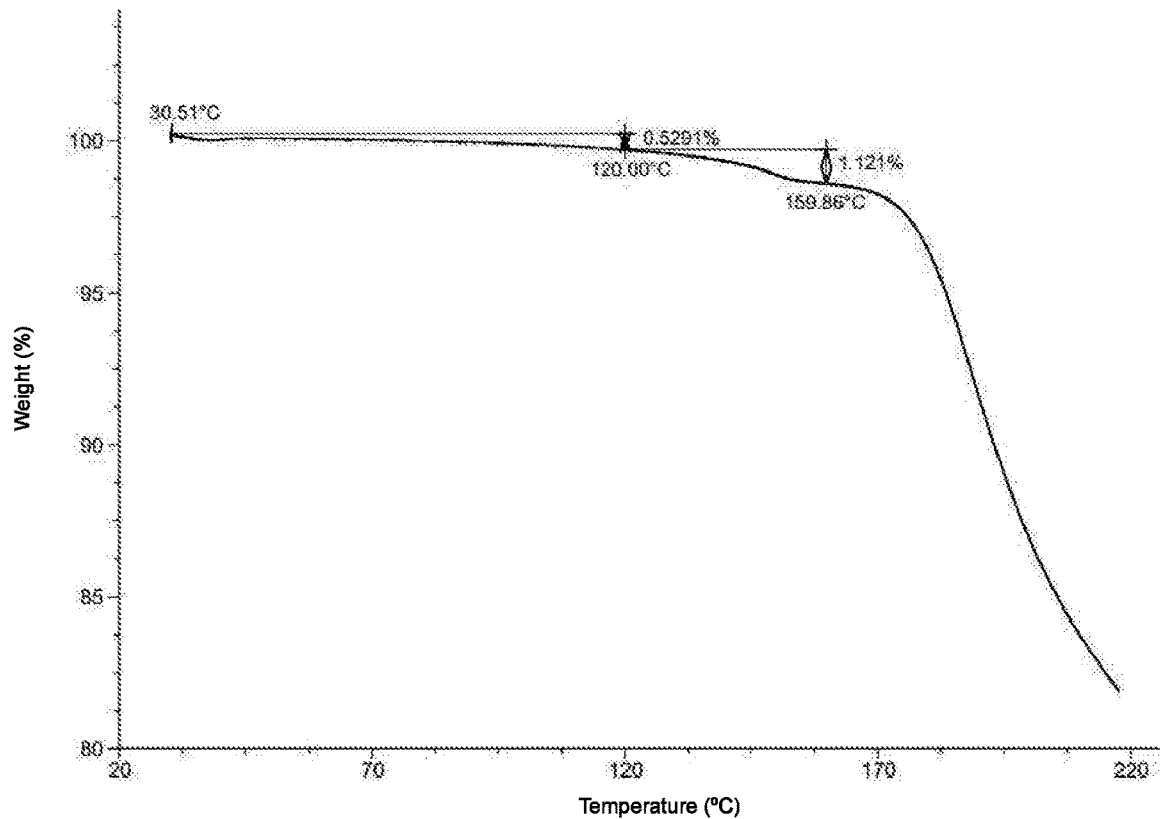
FIG. 14 is a TGA pattern of the crystal form E.

3. The crystal form of Compound 1 according to claim 2, wherein
the crystal form A has an XRPD pattern as shown in FIG. 1;
the crystal form B has an XRPD pattern as shown in FIG. 3;

the crystal form C has an XRPD pattern as shown in FIG. 6;
the crystal form D has an XRPD pattern as shown in FIG. 9;
the crystal form E has an XRPD pattern as shown in FIG. 12.

4. A hydrochloride salt of Formula (I) comprising a crystal form F having an X-ray powder diffraction pattern with characteristic diffraction peaks at angles 2θ of: 11.64±0.2°, 13.32±0.2°, 14.02±0.2°, 20.06±0.2°, 24.22±0.2°

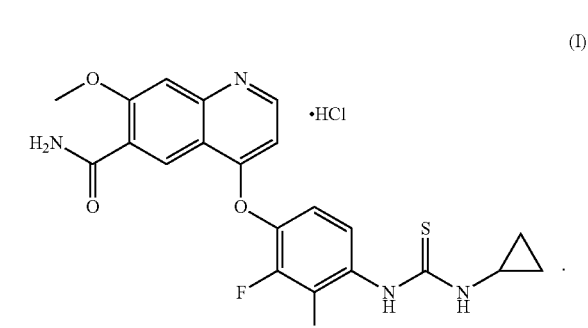

(I)

5. The hydrochloride salt of Formula (I) according to claim 4, wherein the crystal form F further has an X-ray powder diffraction pattern with characteristic diffraction peaks at angles 2θ of: 11.64±0.2°, 13.32±0.2°, 14.02±0.2°, 16.78±0.2°, 20.06±0.2°, 24.22±0.2°, 25.02±0.2°.

Figure 15:
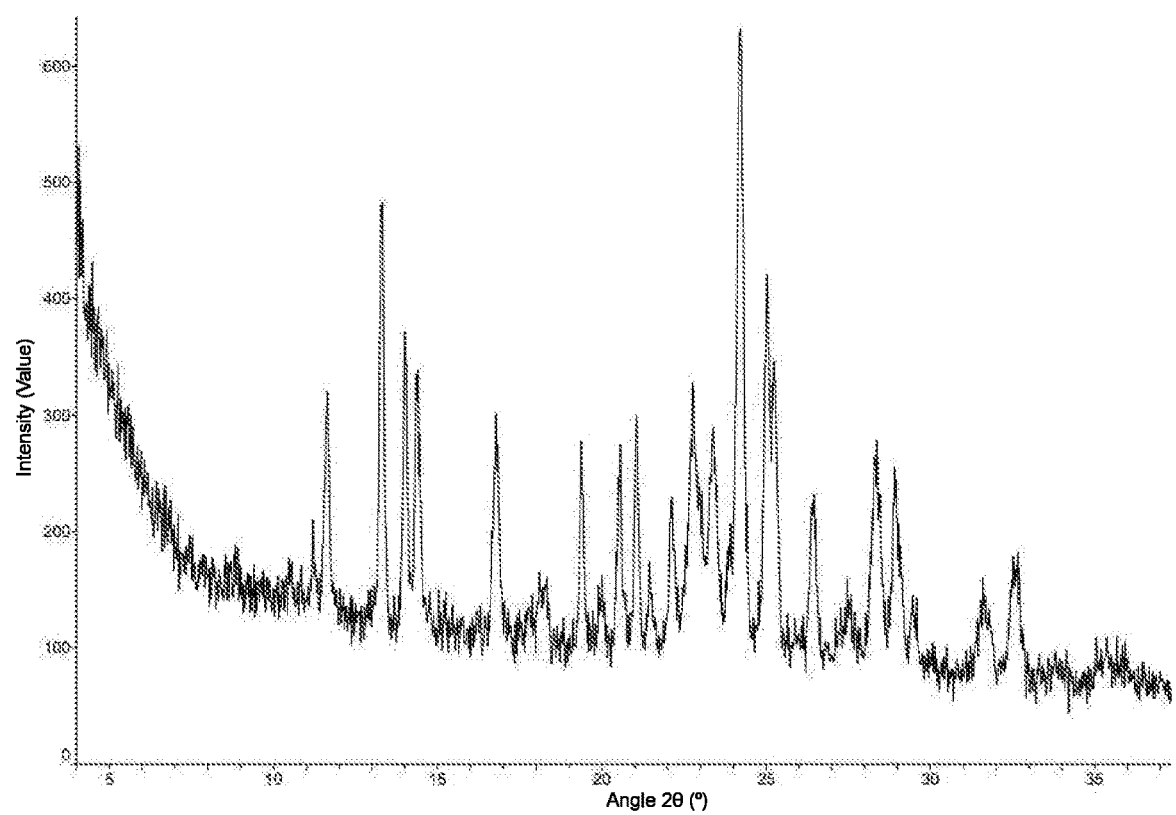
FIG. 15 is an XRPD pattern of the crystal form F with Cu-Kα radiation.
Figure 16:
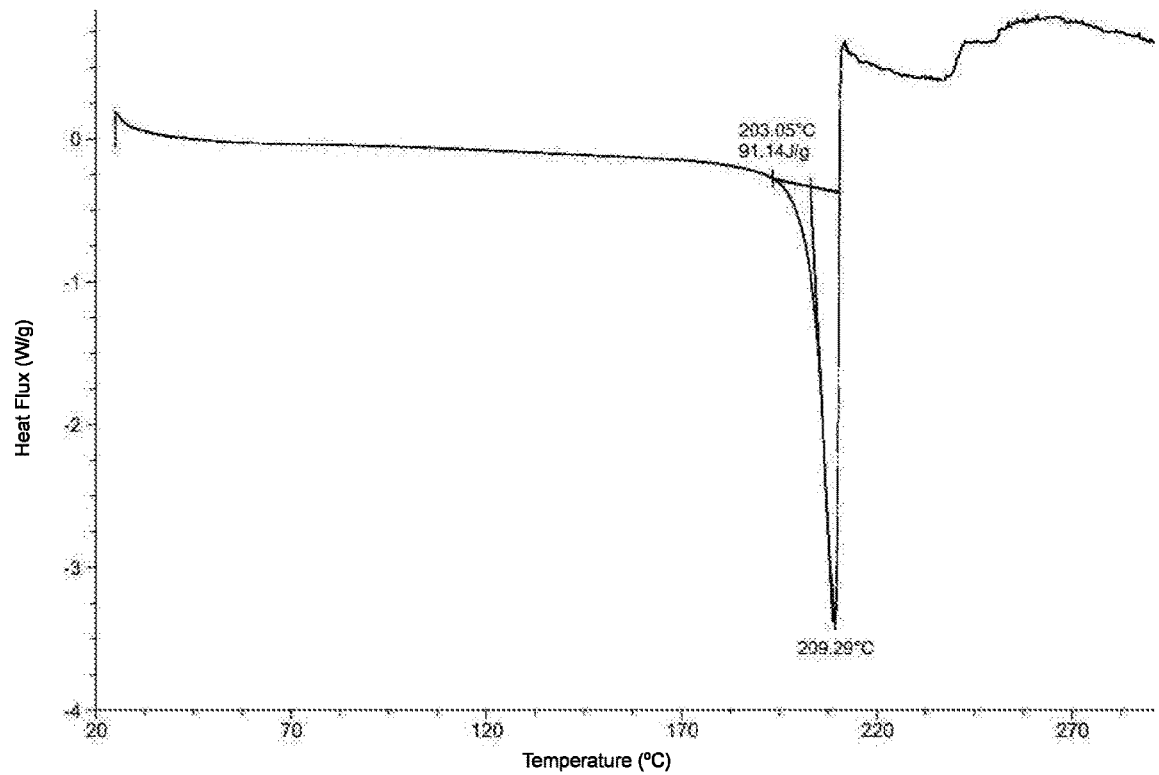
FIG. 16 is a DSC pattern of the crystal form F.
Figure 17:
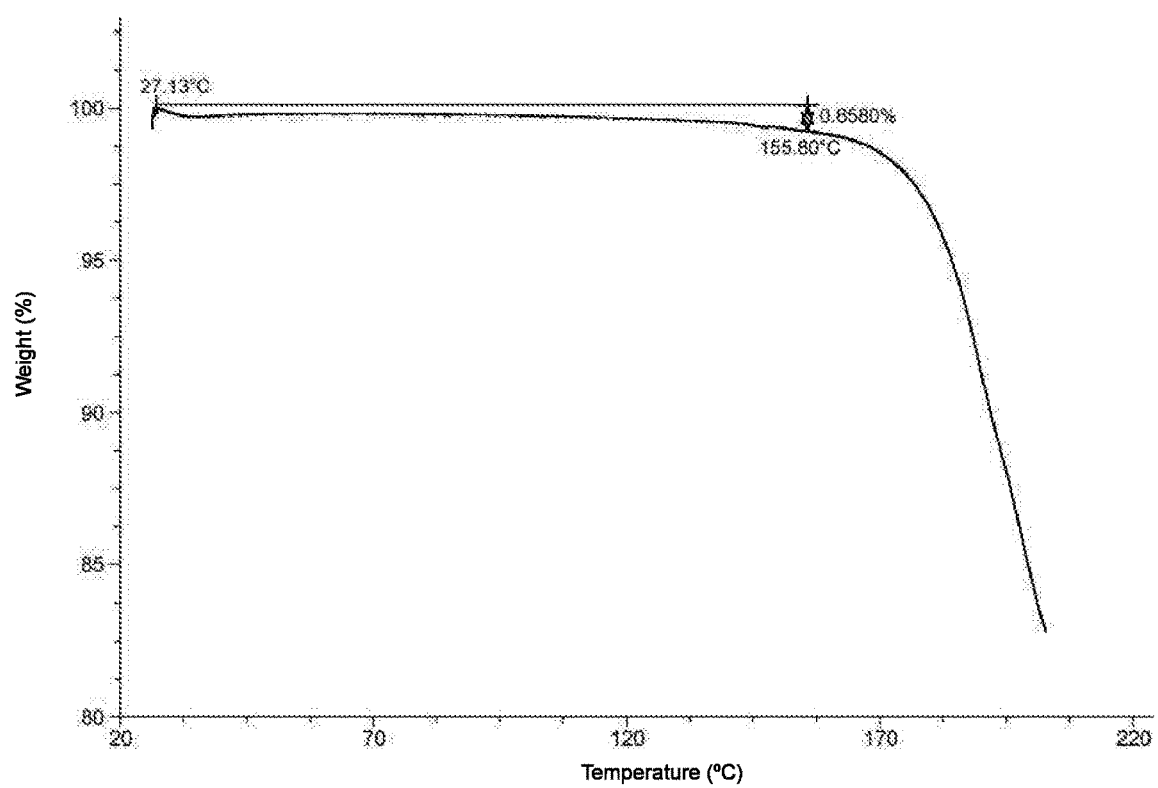
FIG. 17 is a TGA pattern of the crystal form F.

6. The hydrochloride salt of Formula (I) according to claim 5, wherein the crystal form F has an XRPD pattern as shown in FIG. 15.

7. A p-toluenesulfonate salt of Formula (II) comprising a crystal form G having an X-ray powder diffraction pattern with characteristic diffraction peaks at angles 2θ of: 4.84±0.2°, 9.93±0.2°, 15.43±0.2°, 19.48±0.2°, 19.93±0.2°

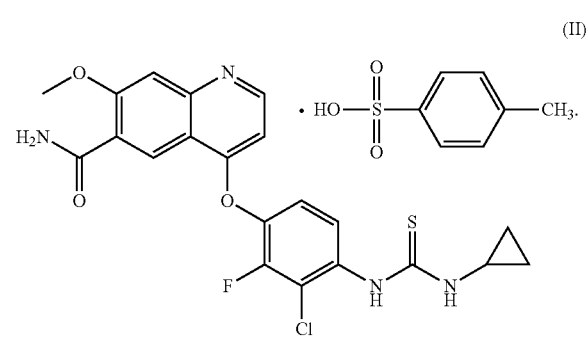

(II)

8. The p-toluenesulfonate salt of Formula (II) according to claim 7, wherein the crystal form G further has an X-ray powder diffraction pattern with characteristic diffraction peaks at angles 2θ of: 4.84±0.2°, 9.93±0.2°, 15.43±0.2°, 19.48±0.2°, 19.93±0.2°, 20.56±0.2°, 24.20±0.2°, 24.89±0.2°.

Figure 18:
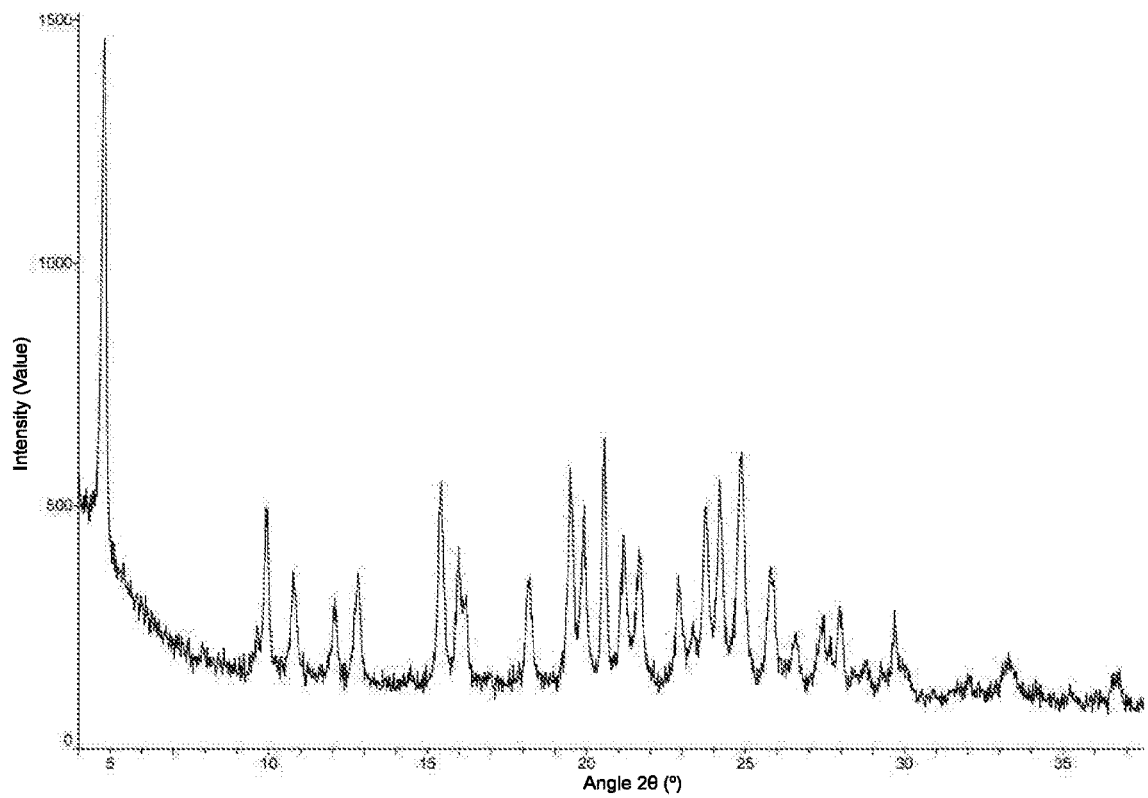
FIG. 18 is an XRPD pattern of the crystal form G with Cu-Kα radiation.
Figure 19:
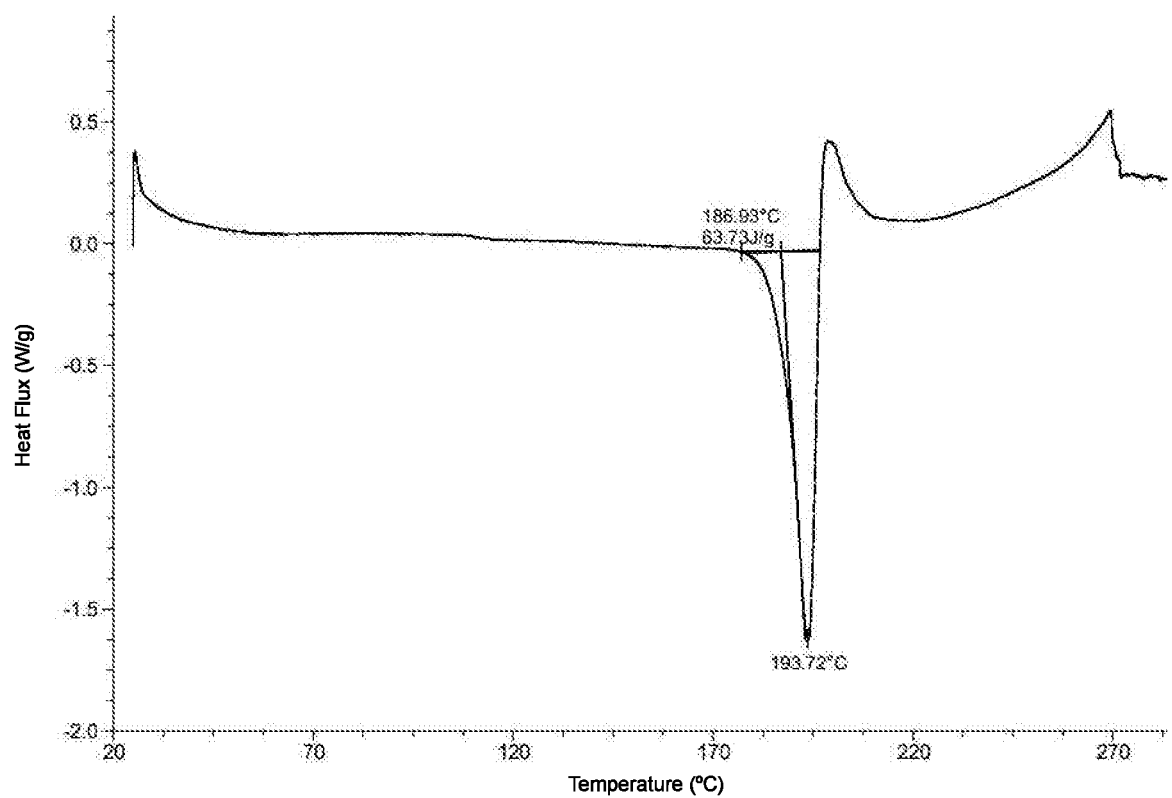
FIG. 19 is a DSC pattern of the crystal form G.
Figure 20:
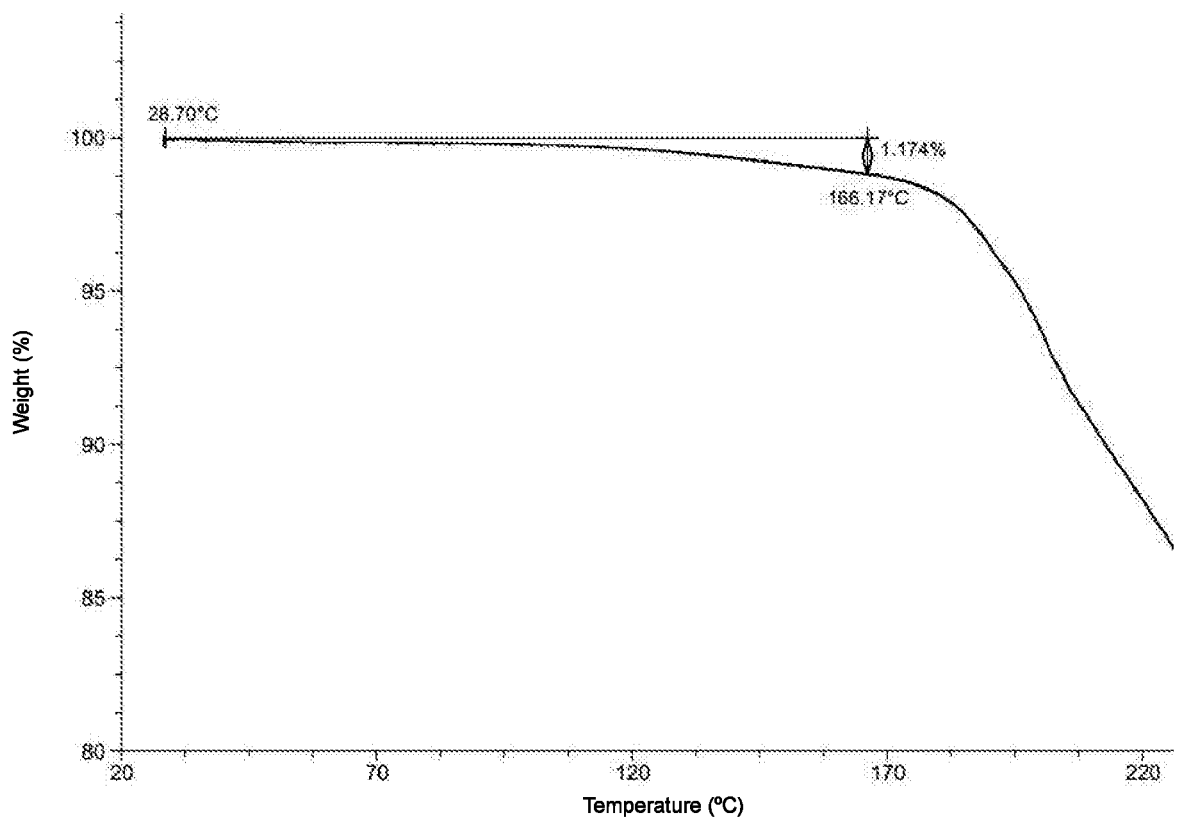
FIG. 20 is a TGA pattern of the crystal form G.

9. The p-toluenesulfonate salt of Formula (II) according to claim 8, wherein the crystal form G has an XRPD pattern as shown in FIG. 18.

10. An ethanesulfonate salt of Formula (III) comprising a crystal form H having an X-ray powder diffraction pattern with characteristic diffraction peaks at angles 2θ of: 7.80±0.2°, 12.53±0.2°, 13.11±0.2°, 17.78±0.2°, 21.90±0.2°

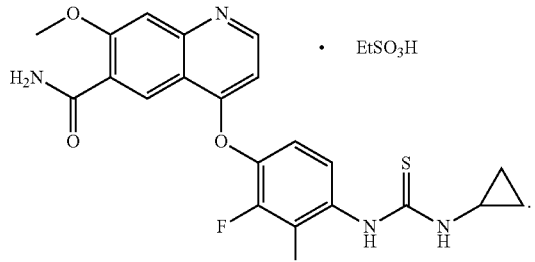

(III)

11. The ethanesulfonate salt of Formula (III) according to claim 10, wherein the crystal form H further has an X-ray powder diffraction pattern with characteristic diffraction peaks at angles 2θ of: 7.80±0.2°, 12.53±0.2°, 13.11±0.2°, 14.86±0.2°, 17.78±0.2°, 20.11±0.2°, 21.90±0.2°.

Figure 21:
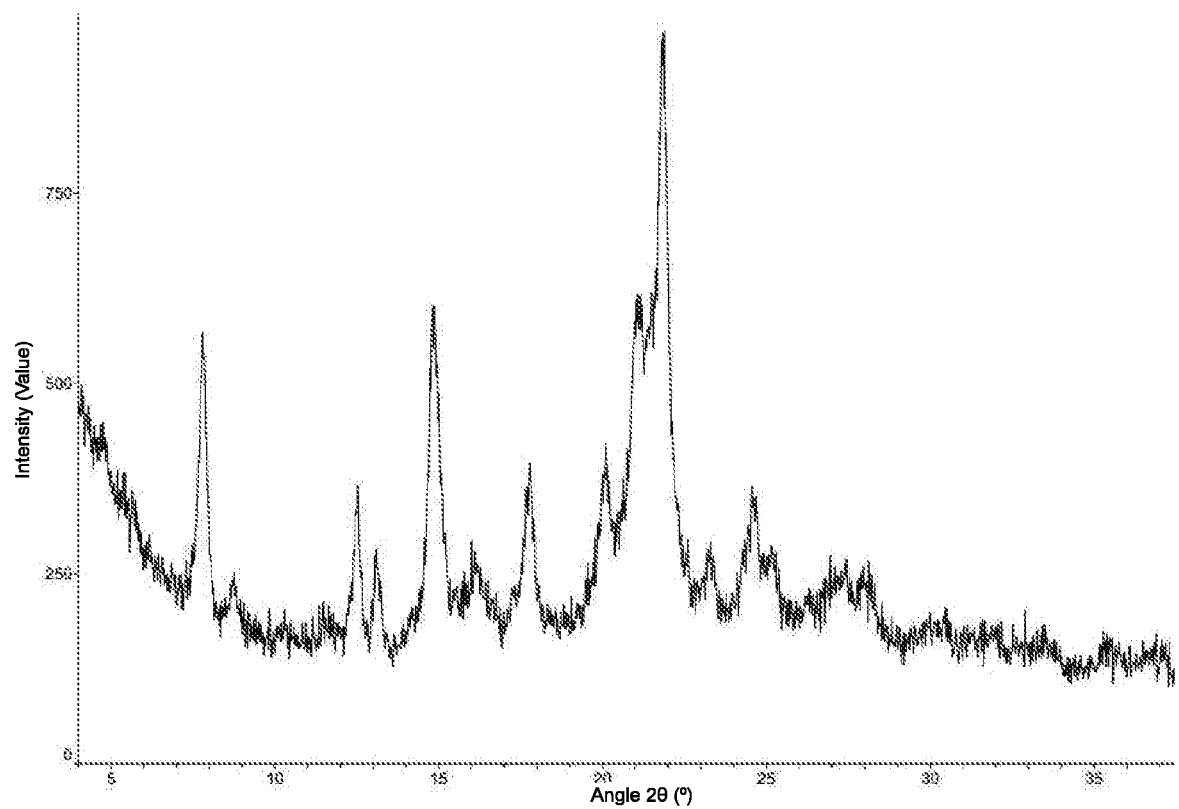
FIG. 21 is an XRPD pattern of the crystal form H with Cu-Kα radiation.
Figure 22:
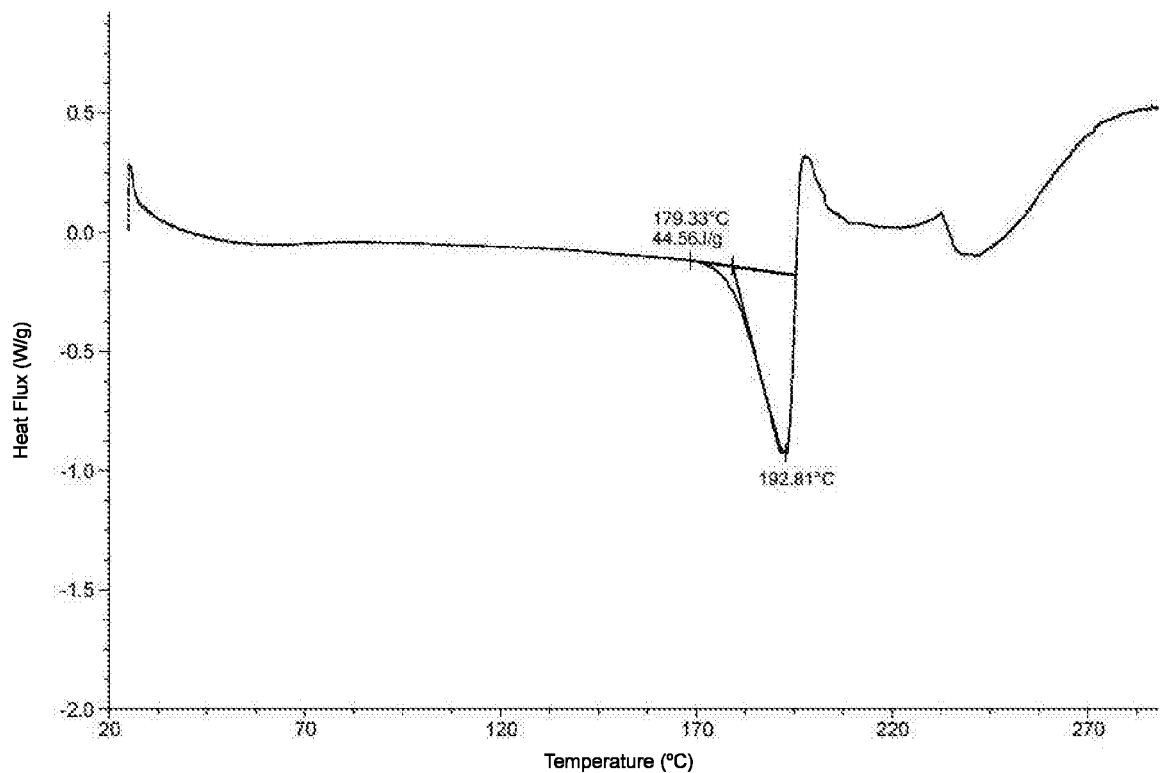
FIG. 22 is a DSC pattern of the crystal form H.
Figure 23:
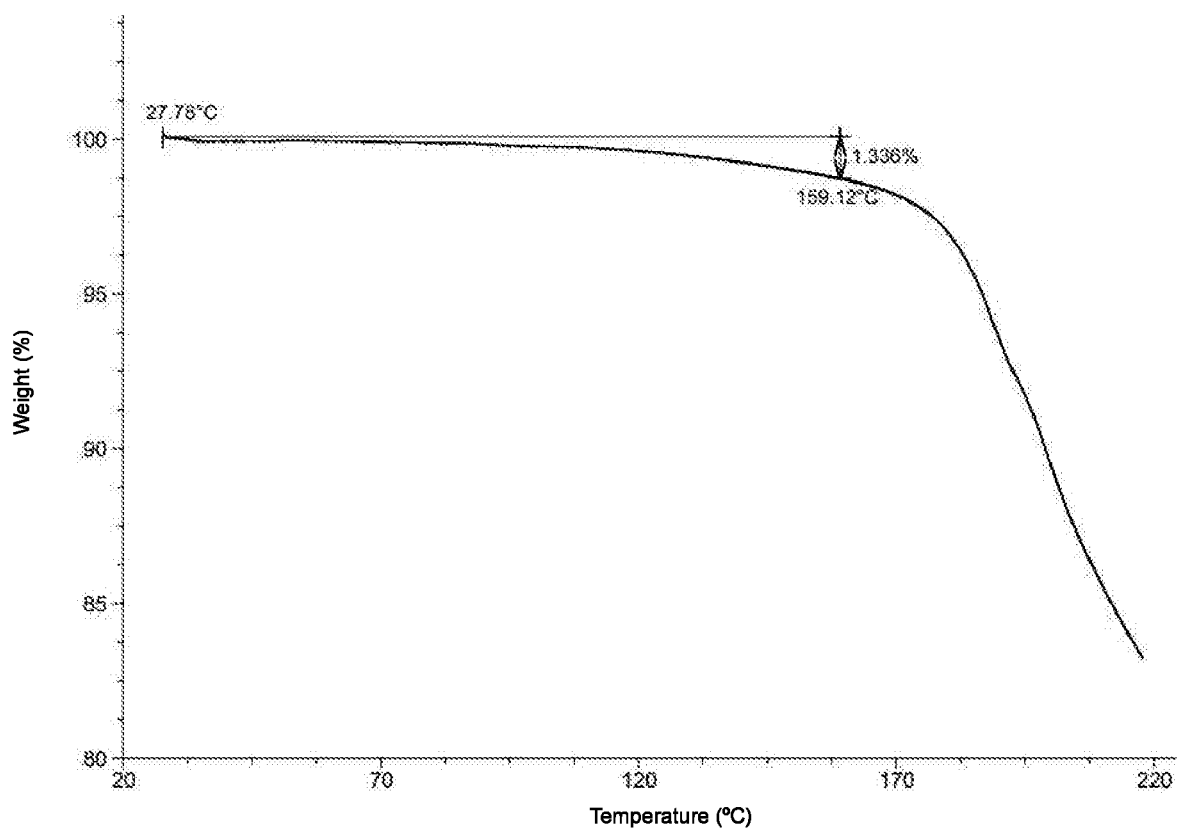
FIG. 23 is a TGA pattern of the crystal form H.

12. The ethanesulfonate salt of Formula (III) according to claim 11, wherein the crystal form H has an XRPD pattern as shown in FIG. 21.

13. A methanesulfonate salt of Formula (IV) comprising a crystal form J, a crystal form K, a crystal form L or a crystal form M, wherein,

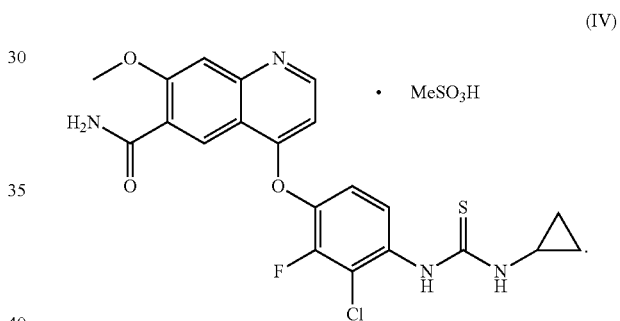

(IV)

the crystal form J has an X-ray powder diffraction pattern with characteristic diffraction peaks at angles 2θ of: 7.88±0.2°, 12.58±0.2°, 15.02±0.2°, 21.28±0.2°, 22.00±0.2°, 27.35±0.2°;
the crystal form K has an X-ray powder diffraction pattern with characteristic diffraction peaks at angles 2θ of: 8.02±0.2°, 16.52±0.2°, 18.10±0.2°, 20.35±0.2°, 22.10±0.2°, 23.27±0.2°;
the crystal form L has an X-ray powder diffraction pattern with characteristic diffraction peaks at angle 2θ of: 18.06±0.2°, 21.35±0.2°, 22.05±0.2°, 24.94±0.2°;
the crystal form M has an X-ray powder diffraction pattern with characteristic diffraction peaks at angles 2θ of: 9.68±0.2°, 20.78±0.2°, 23.15±0.2°, 29.82±0.2°.

14. The methanesulfonate salt of Formula (IV) according to claim 13, wherein,
the crystal form J further has an X-ray powder diffraction pattern with characteristic diffraction peaks at angles 2θ of: 7.88±0.2°, 12.58±0.2°, 15.02±0.2°, 16.42±0.2°, 20.41±0.2°, 21.28±0.2°, 22.00±0.2°, 27.35±0.2°;
the crystal form K further has an X-ray powder diffraction pattern with characteristic diffraction peaks at angles 2θ of: 8.02±0.2°, 15.14±0.2°, 16.52±0.2°, 18.10±0.2°, 20.35±0.2°, 21.36±0.2°, 22.10±0.2°, 23.27±0.2°;
the crystal form L further has an X-ray powder diffraction pattern with characteristic diffraction peaks at angles 2θ of: 8.00±0.2°, 15.10±0.2°, 16.49±0.2°, 18.06±0.2°, 20.49±0.2°, 21.35±0.2°, 22.05±0.2°, 24.94±0.2°;

the crystal form M further has an X-ray powder diffraction pattern with characteristic diffraction peaks at angles 2θ of: 9.68±0.2°, 17.37±0.2°, 18.24±0.2°, 20.19±0.2°, 20.78±0.2°, 22.10±0.2°, 22.74±0.2°, 23.15±0.2°, 29.82±0.2°.

Figure 24:
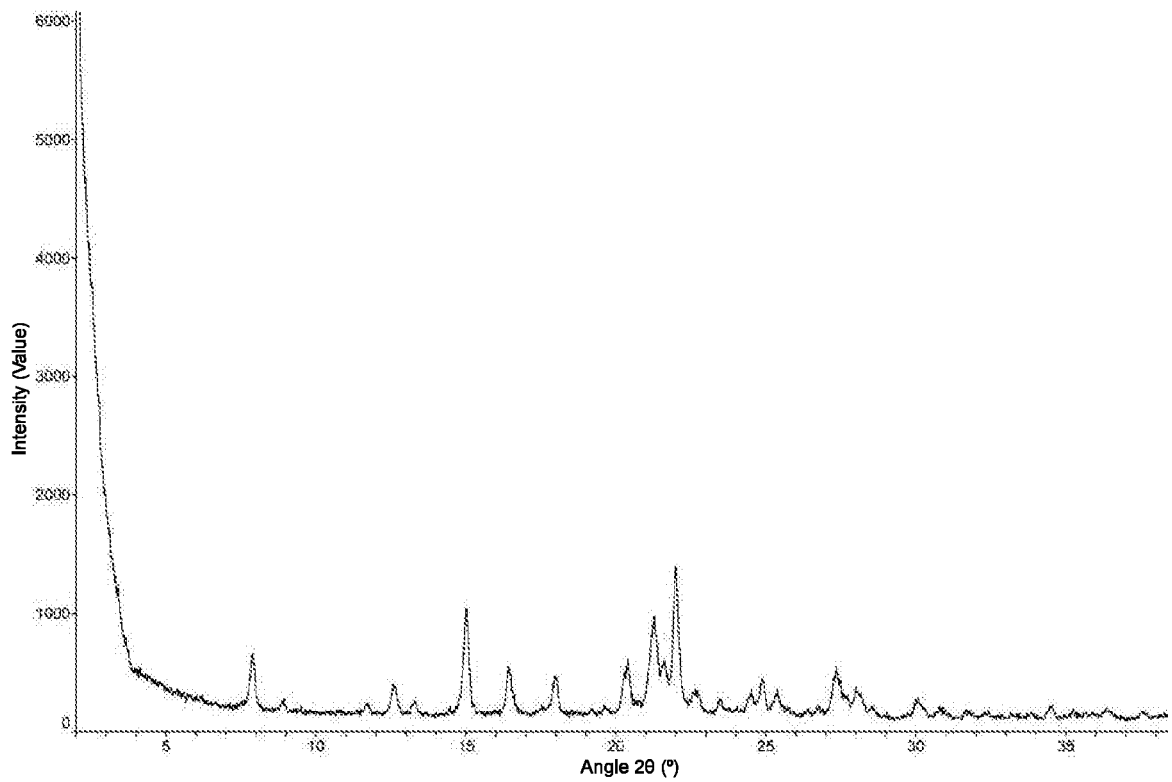
FIG. 24 is an XRPD pattern of the crystal form J with Cu-Kα radiation.
Figure 25:
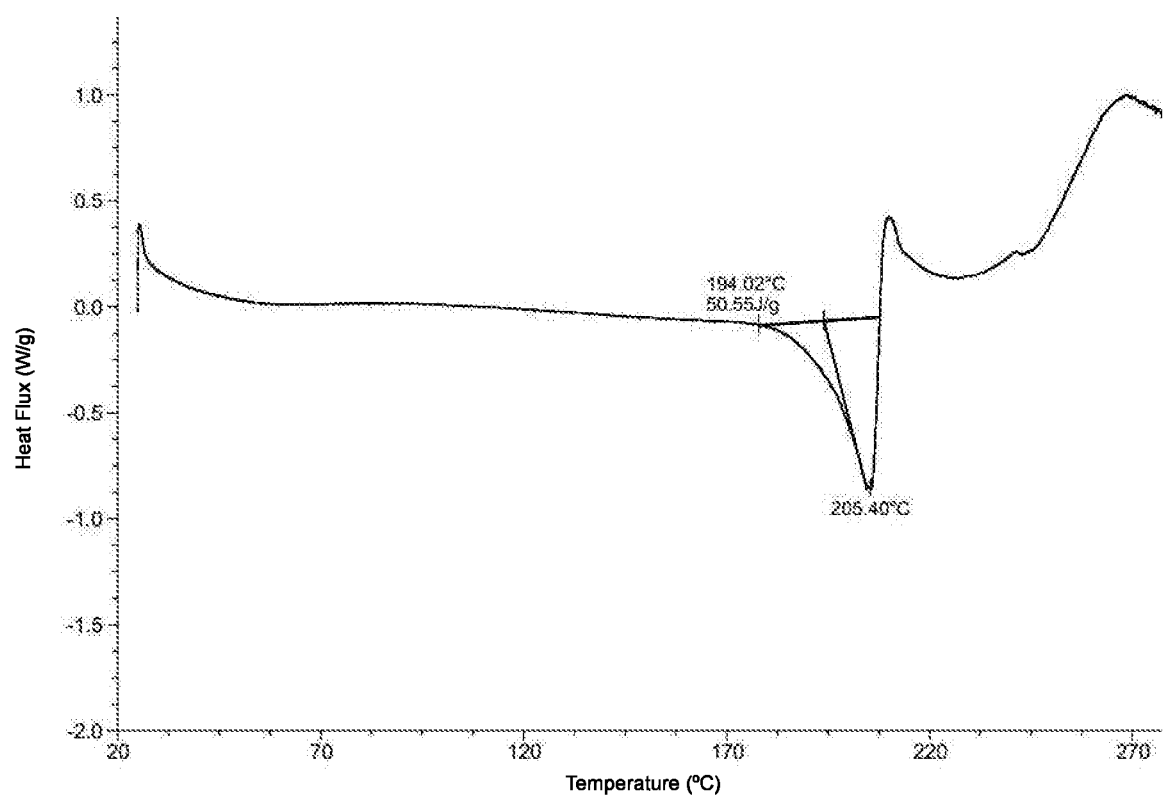
FIG. 25 is a DSC pattern of the crystal form J.
Figure 26:
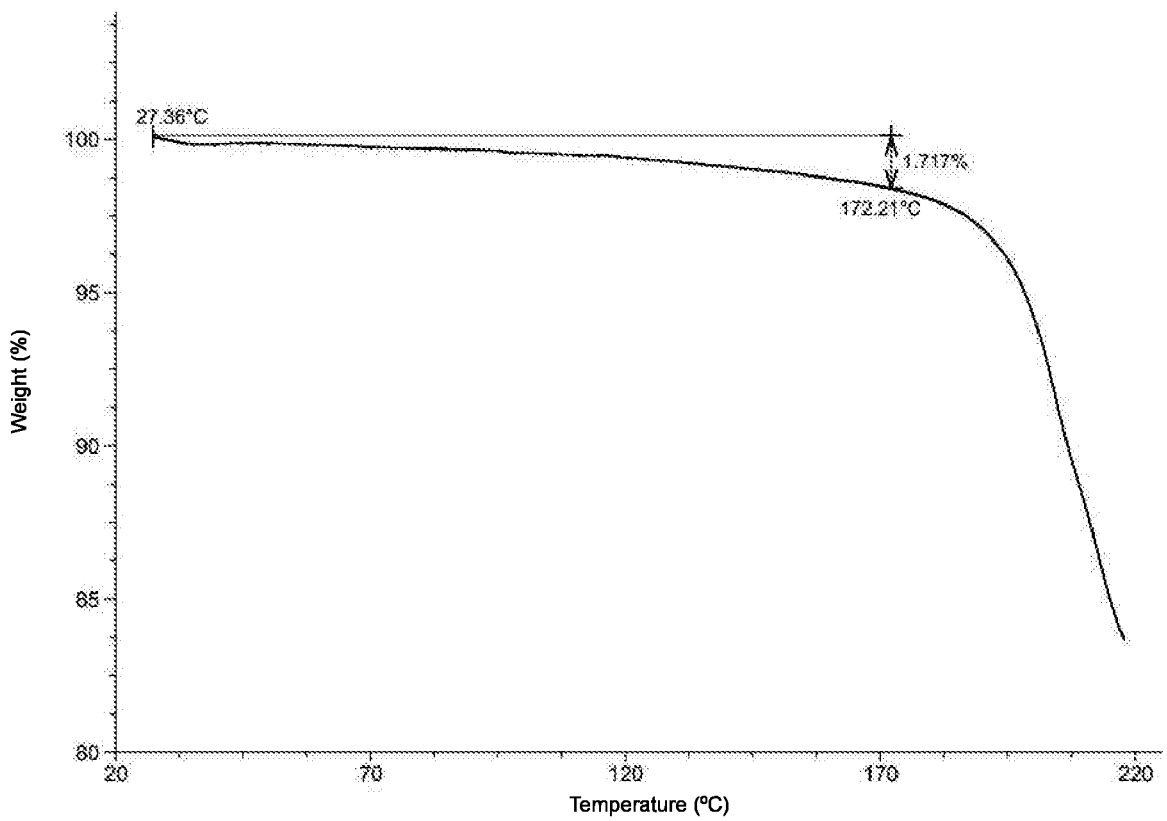
FIG. 26 is a TGA pattern of the crystal form J.
Figure 27:
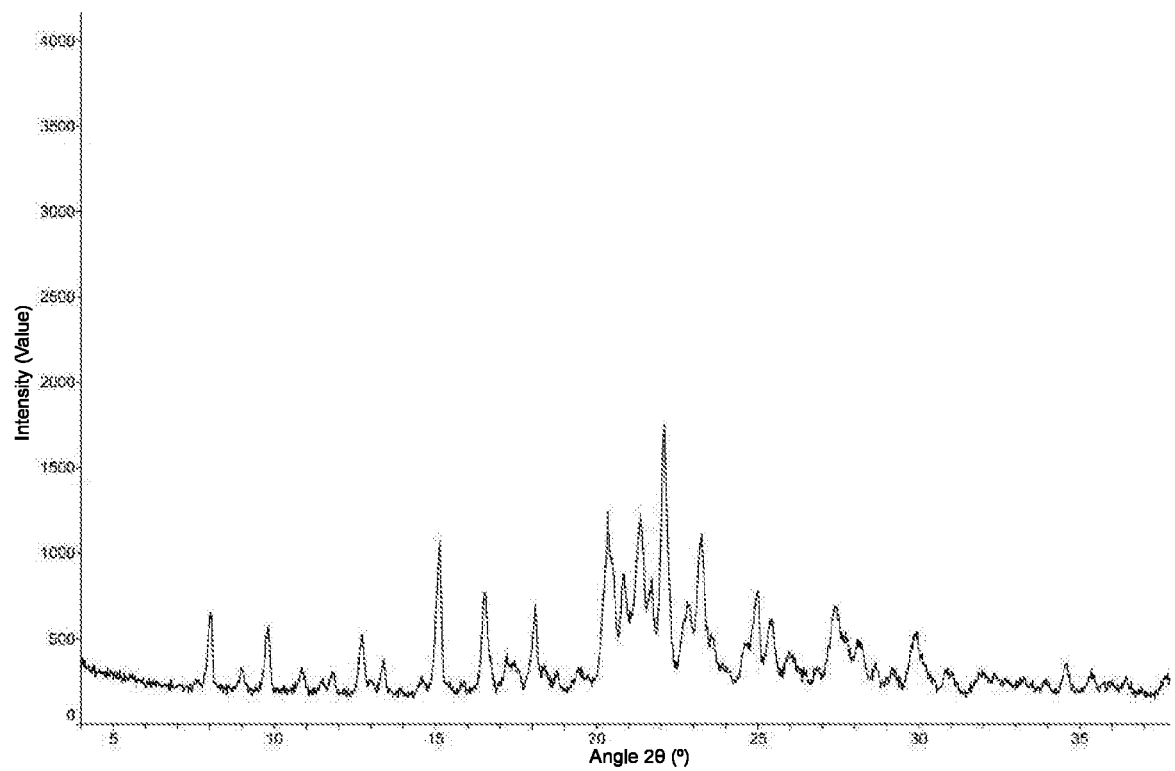
FIG. 27 is an XRPD pattern of the crystal form K with Cu-Kα radiation.
Figure 28:
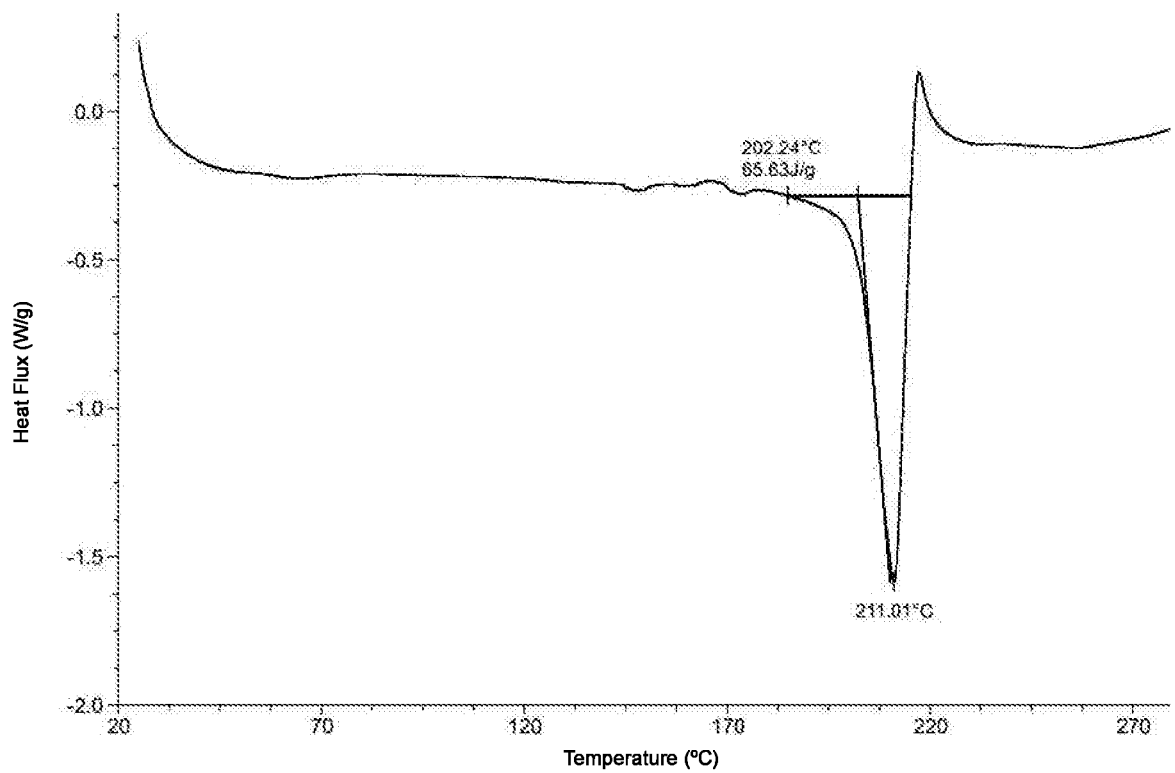
FIG. 28 is a DSC pattern of the crystal form K.
Figure 29:
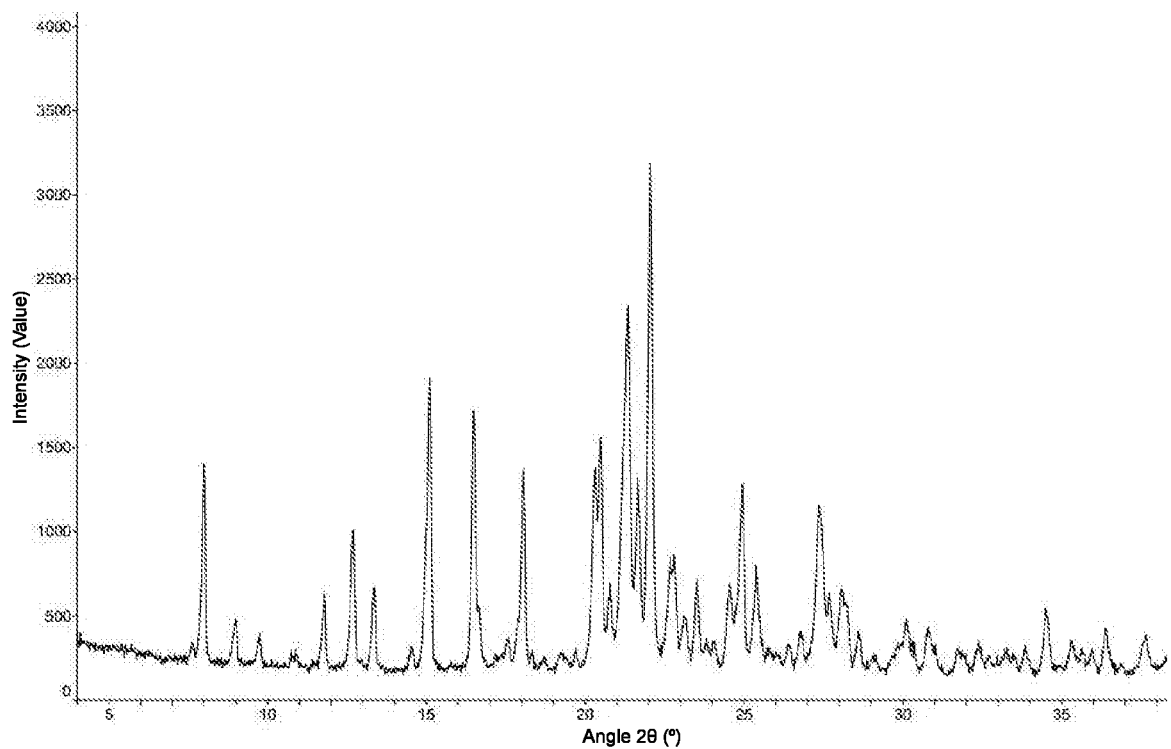
FIG. 29 is an XRPD pattern of the crystal form L with Cu-Kα radiation.
Figure 30:
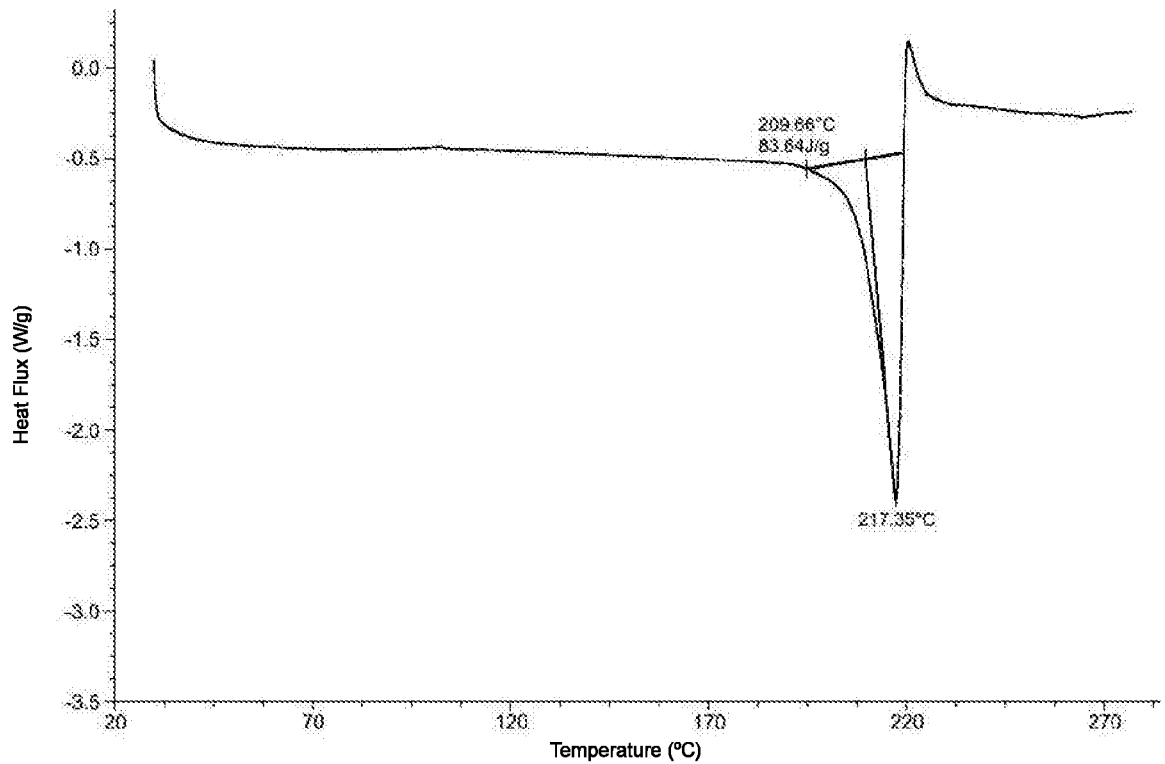
FIG. 30 is a DSC pattern of the crystal form L.
Figure 31:
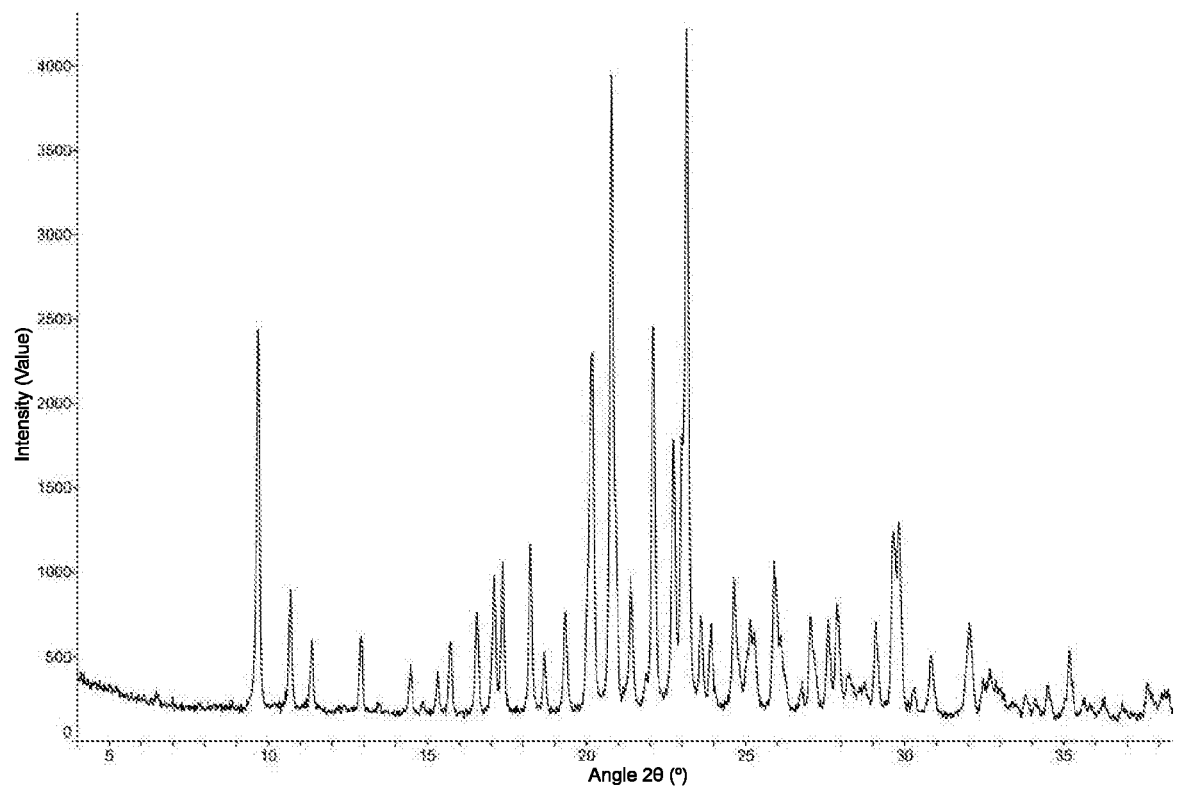
FIG. 31 is an XRPD pattern of the crystal form M with Cu-Kα radiation.
Figure 32:
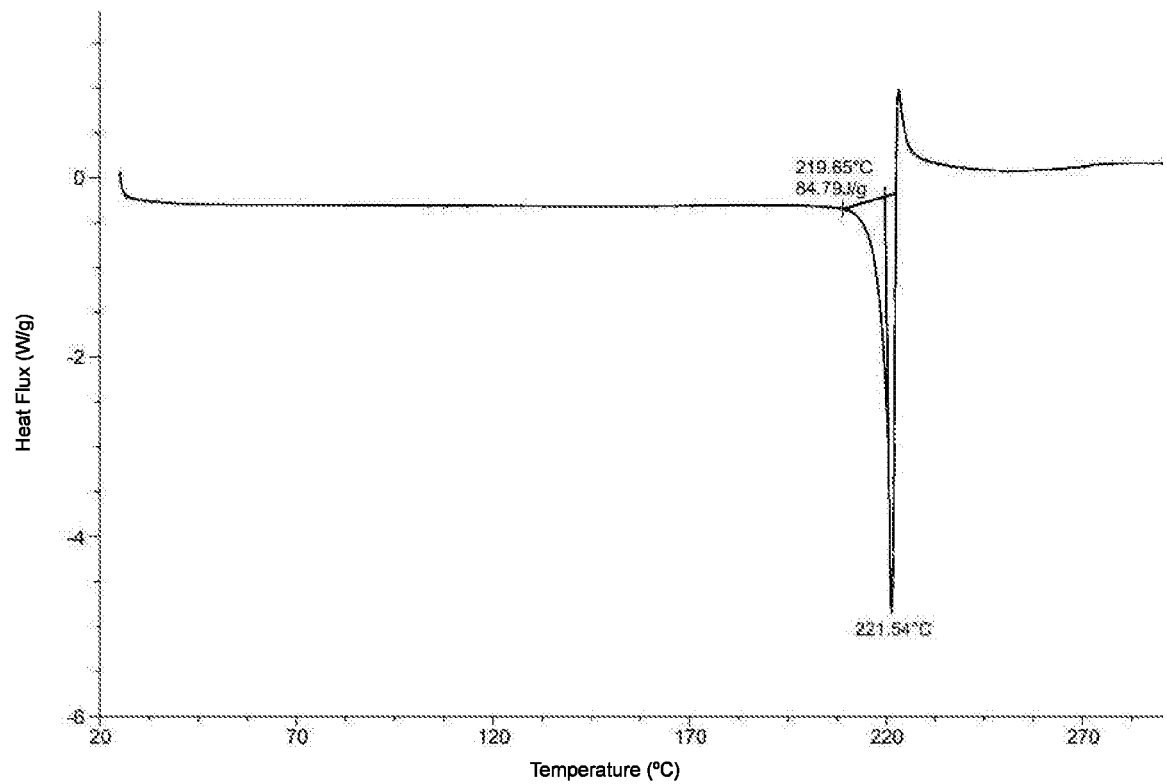
FIG. 32 is a DSC pattern of the crystal form M.

15. The methanesulfonate salt of Formula (IV) according to claim 14, wherein the crystal form J has an XRPD pattern as shown in FIG. 24;

the crystal form K has an XRPD pattern as shown in FIG. 27;

the crystal form L has an XRPD pattern as shown in FIG. 29;

the crystal form M has an XRPD pattern as shown in FIG. 31.

* * * * *